(12) United States Patent
Thomas et al.

(10) Patent No.: US 7,173,038 B1
(45) Date of Patent: Feb. 6, 2007

(54) QUINAZOLINE DERIVATIVES AS VEGF INHIBITORS

(75) Inventors: Andrew Peter Thomas, Macclesfield Cheshire (GB); Elaine Sophie Elizabeth Stokes, Macclesfield Cheshire (GB); Laurent Francois Andre Hennequin, Reims Cedex (FR)

(73) Assignee: AstraZeneca AB, Sodertalje (SE)

(*) Notice: Subject to any disclaimer, the term of this patent is extended or adjusted under 35 U.S.C. 154(b) by 286 days.

(21) Appl. No.: 10/129,336

(22) PCT Filed: Nov. 1, 2000

(86) PCT No.: PCT/GB00/04181

§ 371 (c)(1),
(2), (4) Date: May 3, 2002

(87) PCT Pub. No.: WO01/32651

PCT Pub. Date: May 10, 2001

(30) Foreign Application Priority Data

Nov. 5, 1999 (EP) .................................. 99402759
Nov. 19, 1999 (EP) .................................. 99402877

(51) Int. Cl.
*A61K 31/53* (2006.01)
*A61K 31/517* (2006.01)
*A61K 31/519* (2006.01)
*C07D 239/72* (2006.01)

(52) U.S. Cl. ................. 514/259; 514/245; 514/266.21; 514/266.22; 544/283; 544/293

(58) Field of Classification Search ................ 514/257, 514/245, 266.21, 266.22, 259; 544/283, 544/293
See application file for complete search history.

(56) References Cited

U.S. PATENT DOCUMENTS

| | | | |
|---|---|---|---|
| 3,266,990 A | 8/1966 | Lutz et al. | 514/259 |
| 4,343,940 A | 8/1982 | Kreighbaum et al. | 544/283 |
| 5,373,011 A | 12/1994 | Haley | 514/266.4 |
| 5,409,930 A | 4/1995 | Spada et al. | 514/248 |
| 5,411,963 A | 5/1995 | Dreikorn et al. | 514/266.3 |
| 5,457,105 A | 10/1995 | Barker | 514/234 |
| 5,475,001 A | 12/1995 | Barker | 514/258 |
| 5,480,883 A | 1/1996 | Spada et al. | 514/249 |
| 5,569,658 A | 10/1996 | Barker | 514/250 |
| 5,571,815 A | 11/1996 | Schaper et al. | 514/269 |
| 5,580,870 A | 12/1996 | Barker et al. | 514/234 |
| 5,616,582 A | 4/1997 | Barker | 514/234 |
| 5,639,757 A | 6/1997 | Dow et al. | 514/261 |
| 5,646,153 A | 7/1997 | Spada et al. | 514/259 |
| 5,650,415 A | 7/1997 | Tang et al. | 514/312 |
| 5,656,643 A | 8/1997 | Spada et al. | 514/312 |
| 5,710,158 A | 1/1998 | Myers et al. | 514/259 |
| 5,712,395 A | 1/1998 | App et al. | 544/344 |
| 5,714,493 A | 2/1998 | Myers et al. | 514/259 |
| 5,721,237 A | 2/1998 | Myers et al. | 514/259 |
| 5,736,534 A | 4/1998 | Arnold | 514/63 |
| 5,747,498 A | 5/1998 | Schnur et al. | 514/259 |
| 5,770,599 A | 6/1998 | Gibson | 514/228 |
| 5,770,603 A | 6/1998 | Gibson | 514/259 |
| 5,792,771 A | 8/1998 | App et al. | 514/259 |
| 5,814,630 A | 9/1998 | Barker et al. | 514/234 |
| 5,821,246 A | 10/1998 | Brown et al. | 514/253 |
| 5,866,572 A | 2/1999 | Barker et al. | 514/234 |
| RE36,256 E | 7/1999 | Spada et al. | 514/249 |
| 5,929,080 A | 7/1999 | Frost | 514/266.4 |
| 5,932,574 A | 8/1999 | Barker | 514/234 |
| 5,942,514 A | 8/1999 | Barker | 514/254 |
| 5,952,333 A | 9/1999 | Barker | 514/254 |

(Continued)

FOREIGN PATENT DOCUMENTS

DE 2213558 10/1972

(Continued)

OTHER PUBLICATIONS

Hennequin et al., "Design and Structure Activity Relationship of a New Class of Potent VEGF Receptor Tyrosine Kinase Inhibitors"; Journal of Medicinal Chemistry, American Chemical Society, 1999, vol. 42, pp. 5369-5389 XP002134973, ISSN: 022-2623, example 32.

(Continued)

*Primary Examiner*—James O. Wilson
*Assistant Examiner*—Tamthom N. Truong
(74) *Attorney, Agent, or Firm*—Morgan Lewis & Boclkius LLP

(57) ABSTRACT

The invention relates to quinazoline derivatives of formula (I), wherein m is an integer from 1 to 3; $R^1$ represents halogeno or $C_{1-3}$alkyl; $X^1$ represents —O—; $R^2$ is selected from one of the following three groups: 1) $C_{1-5}$alkyl$R^3$ (wherein $R^3$ is piperidin-4-yl which may bear one or two substituents selected from hydroxy, halogeno, $C_{1-4}$hydroxyalkyl and $C_{1-4}$alkoxy; 2) $C_{2-5}$alkenyl$R^3$ (wherein $R^3$ is as defined hereinbefore); 3) $C_{2-5}$alkynyl$R^3$ (wherein $R^3$ is as defined hereinbefore); and wherein any alkyl, alkenyl or alkynyl group may bear one or more substituents selected from hydroxy, halogeno and amino; and salts thereof, processes for their preparation, pharmaceutical compositions containing a compound of formula (I) or a pharmaceutically acceptable salt thereof as a active ingredient. The compounds of formula (I) and the pharmaceutically acceptable salts thereof inhibit the effects of VEGF, a property of value in the treatment of number of disease states including cancer and rheumatoid arthritis.

11 Claims, No Drawings

U.S. PATENT DOCUMENTS

| | | | |
|---|---|---|---|
| 5,955,464 A | 9/1999 | Barker | 514/254 |
| 5,962,458 A | 10/1999 | Lohmann et al. | 514/266.21 |
| 6,002,008 A | 12/1999 | Wissner et al. | 546/160 |
| 6,015,814 A | 1/2000 | Barker | 514/254 |
| 6,057,320 A | 5/2000 | Spada et al. | 514/249 |
| 6,071,921 A | 6/2000 | Lohmann et al. | 514/266.22 |
| 6,184,225 B1 * | 2/2001 | Thomas et al. | 514/234.5 |
| 6,258,951 B1 | 7/2001 | Lohmann et al. | 544/283 |
| 6,265,411 B1 | 7/2001 | Thomas et al. | 514/266.2 |
| 6,291,455 B1 | 9/2001 | Thomas et al. | 514/231.5 |
| 6,294,532 B1 | 9/2001 | Thomas et al. | 514/228.2 |
| 6,362,336 B1 | 3/2002 | Lohmann et al. | 544/283 |
| 6,414,148 B1 * | 7/2002 | Thomas et al. | 544/283 |
| 6,514,971 B1 | 2/2003 | Thomas et al. | 514/234.5 |
| 6,645,969 B1 | 11/2003 | Myers et al. | 514/230.5 |
| 6,673,803 B2 | 1/2004 | Thomas et al. | 514/263.4 |
| 6,809,097 B1 | 10/2004 | Thomas et al. | 514/235.2 |
| 6,887,874 B2 | 5/2005 | Hennequin | 514/248 |
| 6,897,210 B2 | 5/2005 | Thomas et al. | 514/183 |
| 2003/0086924 A1 * | 5/2003 | Sliwkowski | 424/143.1 |
| 2003/0144298 A1 | 7/2003 | Curwen et al. | 514/252.17 |
| 2003/0191308 A1 | 10/2003 | Hennequin et al. | 544/60 |
| 2003/0199491 A1 | 10/2003 | Hennequin | 514/210.21 |
| 2003/0199513 A1 | 10/2003 | Thomas et al. | 514/248 |
| 2003/0207878 A1 | 11/2003 | Hennequin | 514/228.2 |
| 2003/0225111 A1 | 12/2003 | Hennequin et al. | 514/260.1 |
| 2005/0043395 A1 | 2/2005 | Wedge | 514/449 |
| 2005/0085465 A1 | 4/2005 | Hennequin | 514/227.8 |
| 2005/0222183 A1 | 10/2005 | Wedge | 514/266.22 |
| 2005/0239777 A1 | 10/2005 | Thomas et al. | 514/227.8 |
| 2005/0245549 A1 | 11/2005 | Wedge | 514/266.22 |
| 2006/0004017 A1 | 1/2006 | Stokes et al. | 514/252.17 |
| 2006/0009418 A1 | 1/2006 | Barge | 514/49 |

FOREIGN PATENT DOCUMENTS

| | | |
|---|---|---|
| DE | 2936705 | 3/1980 |
| DE | 19521386 | 12/1996 |
| DE | 19608588 | 9/1997 |
| DE | 19608631 | 9/1997 |
| DE | 19608653 | 9/1997 |
| DE | 19614718 | 10/1997 |
| DE | 19629652 | 1/1998 |
| EP | 0326307 A2 | 2/1989 |
| EP | 0326330 | 8/1989 |
| EP | 0520722 | 12/1992 |
| EP | 0 566 226 A | 10/1993 |
| EP | 0602851 A1 | 6/1994 |
| EP | 0635498 | 1/1995 |
| EP | 0635507 A1 | 1/1995 |
| EP | 0682027 A1 | 11/1995 |
| EP | 0743308 | 11/1996 |
| EP | 0787722 A1 | 8/1997 |
| EP | 0795556 | 9/1997 |
| EP | 0837063 A1 | 4/1998 |
| GB | 2033894 | 5/1980 |
| GB | 2160201 | 12/1985 |
| JP | 54-2327 | 4/1979 |
| WO | WO 87/04321 | 7/1987 |
| WO | WO 92/14716 | 9/1992 |
| WO | WO 92/16527 | 10/1992 |
| WO | WO 92/20642 | 11/1992 |
| WO | WO 95/06648 | 3/1995 |
| WO | WO 95/15758 | 6/1995 |
| WO | WO 95/15952 | 6/1995 |
| WO | WO 95/19169 | 7/1995 |
| WO | WO 95/19774 | 7/1995 |
| WO | WO 95/19970 | 7/1995 |
| WO | WO 95/21613 | 8/1995 |
| WO | WO 95/23141 | 8/1995 |
| WO | WO 95/24190 | 9/1995 |
| WO | WO 96/07657 | 3/1996 |
| WO | WO 96/09294 | 3/1996 |
| WO | WO 96/15118 | 5/1996 |
| WO | WO 96/16960 | 6/1996 |
| WO | WO 96/29331 | 9/1996 |
| WO | WO 96/30347 | 10/1996 |
| WO | WO 96/30370 | 10/1996 |
| WO | WO 96/31510 | 10/1996 |
| WO | WO 96/33977 | 10/1996 |
| WO | WO 96/33978 | 10/1996 |
| WO | WO 96/33979 | 10/1996 |
| WO | WO 96/33980 | 10/1996 |
| WO | WO 96/33981 | 10/1996 |
| WO | WO 96/34867 | 11/1996 |
| WO | WO 96/35689 | 11/1996 |
| WO | WO 96/39145 | 12/1996 |
| WO | WO 96/40142 | 12/1996 |
| WO | WO 96/40648 | 12/1996 |
| WO | WO 96/40673 | 12/1996 |
| WO | WO 97/02266 | 1/1997 |
| WO | WO 97/03069 | 1/1997 |
| WO | WO 97/13760 | 4/1997 |
| WO | WO 97/13771 | 4/1997 |
| WO | WO 97/14691 | 4/1997 |
| WO | WO 97/16435 | 5/1997 |
| WO | WO 97/17329 | 5/1997 |
| WO | WO 97/18212 | 5/1997 |
| WO | WO 97/22596 | 6/1997 |
| WO | WO 97/28161 | 8/1997 |
| WO | WO 97/30034 | 8/1997 |
| WO | WO 97/30035 | 8/1997 |
| WO | WO 97/30044 | 8/1997 |
| WO | WO 97/32856 | 9/1997 |
| WO | WO 97/34876 | 9/1997 |
| WO | WO 97/37999 | 10/1997 |
| WO | WO 97/38983 | 10/1997 |
| WO | WO 97/38994 | 10/1997 |
| WO | WO 97/42187 | 11/1997 |
| WO | WO 97/49688 | 12/1997 |
| WO | WO 97/49689 | 12/1997 |
| WO | WO 98/02434 | 1/1998 |
| WO | WO 98/02437 | 1/1998 |
| WO | WO 98/02438 | 1/1998 |
| WO | WO 98/07726 | 2/1998 |
| WO | WO 98/10767 | 3/1998 |
| WO | 98-13354 * | 4/1998 |
| WO | WO 98/13350 | 4/1998 |
| WO | WO 98/13354 | 4/1998 |
| WO | WO 98/14431 | 4/1998 |
| WO | WO 98/23613 | 6/1998 |
| WO | WO 98/35958 | 8/1998 |
| WO | WO 98/43960 | 10/1998 |
| WO | WO 98/50038 | 11/1998 |
| WO | WO 99/06378 | 2/1999 |
| WO | WO 99/06396 | 2/1999 |
| WO | WO 99/09016 | 2/1999 |
| WO | WO 99/09024 | 2/1999 |
| WO | WO 99/10349 | 3/1999 |
| WO | WO 00/21955 | 4/2000 |
| WO | WO 00/47212 | 8/2000 |
| WO | WO 01/32651 | 5/2001 |
| WO | WO 01/66099 | 9/2001 |
| WO | WO 01/74360 | 10/2001 |
| WO | WO 01/77085 | 10/2001 |
| WO | WO 02/12226 | 2/2002 |
| WO | WO 02/12227 | 2/2002 |
| WO | WO 02/12228 | 2/2002 |
| WO | WO 03/039551 | 5/2003 |
| WO | WO 03/064413 | 8/2003 |
| WO | WO 04/014383 | 2/2004 |
| WO | WO 04/014426 | 2/2004 |
| WO | WO 04/032937 | 4/2004 |

| WO | WO 04/071397 | 8/2004 |

OTHER PUBLICATIONS

Arya et al., Nitroimidazoles: Part XVI—Some 1-Methyl-4-nitro-5-substituted Imidazoles, Indian Journal of Chemistry, vol. 21B, Dec. 1982, pp. 1115-1117.

Bridges, "The current status of tyrosine kinase inhibitors . . . ," Exp.Opin.Ther.Patents (1995), 5(12): 1245-1257, Editorial, Oncologic, Endocrine & Metabolic, 1995 Ashley Publications Ltd ISSN 1354-3776.

Bridges, et al., "Enantioselective Inhibition of the Epidermal Growth Factor Receptor Tyrosine Kinase by a 4-(a-Phenethylamino)quinazolines," Bioorganic & Medicinal Chemistry, vol. 3, No. 12, pp. 1651-1656, 1995.

Buchdunger, et al., "4,5-Dianilinophthalimide: A protein-tyrosine kinase inhibitor with selectivity for the epidermal growth factor . . . ," Proc.Natl.Acad.Sci., USA, vol. 91, pp. 2334-2338, Mar. 1994, Applied Biological Sciences.

Burke, Jr., "Protein-tyrosine kinase inhibitors," Drugs of the Future 1992, vol. 17(2), pp. 119-131.

Connolly, et al., "Human Vascular Permeability Factor," J.Bio. Chem., vol. 264, No. 33, Nov. 1989, pp. 20017-20024.

Cullinan-Bove, et al., "Vascular Endothelial Growth Factor/Vascular Permeability Factor Expression in the Rat Uterus . . . ," Endocrinology, vol. 133, No. 2, 1993, pp. 829-837.

Dolle, et al., "5,7-Dimethoxy-3-(4-pyridinyl)quinoline Is a Potent and Selective Inhibitor of Human Vascular b-Type Platelet-Derived Growth Factor Receptor Tyrosine Kinase," J.Med.Chem. 1994, vol. 37, pp. 2627-2629.

Fan, et al., "Controlling the Vasculature: Angiogenesis, Anti-Angiogenesis . . . ," TiPS Review, vol. 16, Feb. 1995, pp. 57-65.

Folkman, "Angiogenesis in Cancer, Vascular, Rheumatoid and Other Disease," Nature Medicine, vol. 1, No. 1, 1995, pp. 27-30.

Fry et al., "A Specific Inhibitor of the Epidermal Growth Factor Receptor Tyrosine Kinase," Science, vol. 265, Aug. 19, 1994, pp. 1093-1095.

Gazit et al., Tyrophostins IV—Highly Potent Inhibitors . . . Relationship Study of 4-Anilidoquinazolines, Bioorganic & Medicinal Chemistry, vol. 4, No. 8, 1996, pp. 1203-1207.

Golovkin et al., Nauchin TR-VSES-Nauchno-Issled Inst Farm, 1990, 28, 70-75.

Hara et al., On the Amination of Azaheterocycles. A New Procedure for the Introduction of an Amino Group (1), J. Heterocyclic Chem. vol. 19, 1982, pp. 1285-1287.

Higashino et al., Reactions of the Anion Reissert Compound . . . with Electrophiles, Chem. Pharm. Bull., vol. 33(3), 1985, pp. 950-961.

Iyer, et al., "Studies in Potential Amoebicides: Part III—Synthesis of 4-Substituted Amino-8-Hydroxy) Quinazolines & 3-Substituted 8-Hydroxy(&8-Methoxy)-4-Quinazolones," J.Sci.Industr.Res., vol. 15C, Jan. 1956, pp. 1-7.

Jakeman, et al., "Developmental Expression of Binding Sites and Messenger Ribonucleic Acid . . . ," Endocrinology, vol. 133, No. 2, 1993, pp. 848-859.

Karminski et al., The Synthesis of Some Quinazoline Derivatives and Their Biological Properties; J. Environ. Sci. Health, vol. B18, 1993, pp. 599-610.

Kim, et al., "Inhibition of Vascular Endothelial Growth Factor-Induced Angiogenesis Suppresses Tumour Growth in Vivo," Nature, vol. 362, Apr. 1993, pp. 841-844.

Klohs, Wayne D. et al. "Antiangiogenic Agts.", Curr. Opin. Biotech. 10/6.544-49, Jun. 1999.

Kobayashi, Derwent Abstract 82-87077, vol. 6, No. 244, Dec. 1982, JP 57-144266, Sep. 1982, "4-Anilinoquinazoline Derivative, its Preparation and Analgesic and Antiphlogistic Agent Containing Said Derivative as Active Component". (n7).

Kolch et al., "Regulation of the Expression of the VEGF/VPS and its Receptors: Role in Tumor Angiogenesis," Breast Cancer Research and Treatment, vol. 36, 1995, pp. 139-155.

Kumar et al., Reactions of Diazines with Nucleophiles—IV.1 The Reactivity . . . Single Electron Transfer Reactions, Bioorganic & Medicinal Chemistry, vol. 3, No. 7, 1995, pp. 891-897.

Kyorin, Derwent Abstract 84-53835, JP 59-13765, Jan. 1984, "2-(4-Quinazolinyl)amino benzoic acid derivs . . . having analgesic and antiinflammatory activities", (n.8).

Li, et al., Chem.Abs., vol. 92:76445u, 1980, p. 674-675.

Lin et al., Chem.Abs., vol. 96:122728w, 1982, p. 695.

Maguire, et al., "A New Series of PDGF Receptor Tyrosine Kinase Inhibitors: 3-Substituted Quinoline Derivatives," J.Med.Chem. 1994, vol. 37, pp. 2129-2137.

Nagarajan et al., Nitroimidazoles: Part XIX.dagger.—Structure Activity Relationships.dagger-dbl., Indian Journal of Chemistry, vol. 23B, Apr. 1984, pp. 342-362.

Nomoto et al., Studies on Cardiotonic Agents. VII.1) Potent Cardiotonic Agents KF15232 with Myofibrillar CA2+ Sensitizing Effect, Chem. Pharm. Bull., vol. 39(4), 1991, pp. 900-910.

Rewcastle et al., "Tyrosine Kinase Inhibitors . . . 4-(Phenylamino)quinazolines as Potent . . . Inhibitors of the Tyrosine Kinase Domain of the Epidermal Growth Factor Receptor," J.Med.Chem. 1995, vol. 38, pp. 3482-3487.

Sankyo and Ube, Derwent Abstract 81-28290, JP 56-20577, Feb. 1981, "4-(N-alkyl:anilino) quinazoline derivs . . . having analgesic and antiinflammatory actions". (n.9).

Schonowsky et al., Chinazolinderivative, ihre Herstelhung und biologische Wirkung, Quinzaolines, their Preparation and Biological Activity, Z. Naturforsch, 37b, 1982, pp. 907-911.

Senger, et al., "Vascular Permeability Factor (VPF, VEGF) in Tumor Biology," Cancer and Metastasis Reviews, vol. 12, 1993, pp. 303-324.

Sinyak, et al., Synthesis and Biological Properties of Derivatives of 4-Heterylmercaptoquinazoline, Zaporozh'e Medical Institute pp. 103-106, translated from Khimiko-farmatsevticheskii Zhurnal, vol. 20, No. 2, Feb. 1986, 168-171, original article submitted Dec. 29, 1984.

Spada, et al., Small molecule inhibitors of tyrosine Kinase activity, Exp.Opin.Ther.Patents (1995), 5(8):805-817, Patent Update, Oncologic, Endocrine & Metabolic, Ashley Publications Ltd. ISSN 1354-3776.

Spence, "Inhibitors of Tyrosine Kinase Activity as Anticancer Therapeutics: Recent Developments," Expert Opinion in Therapeutic Patents, Jan. 1993, Patent Update, Anticancers, etc., pp. 3-9, Current Drugs Ltd ISSN 0962-2594.

Stets et al., Investigation of Anti-Arrhythmic Action of Quinazopyrine, Pharmacology Dept., Zaporozhye Medical Institute, Zaporozhye, and Vinnitsa Medical Institute, Vinnitsa, pp. 94-96, translated from Farmakol. 1 toksik, vol. 53, No. 3, 1990, pp. 15-17.

Traxler, et al., "Recent advances in protein tyrosine kinase inhibitors," Drugs of the Future 1995, vol. 20(12, pp. 1261-1274.

Trinks, et al., "Dianilinophthalimides: Potent and Selective, ATP-Competitive Inhibitors of the EGF-Receptor Protein Tyrosine Kinase," J.Med. Chem. 1994, vol. 37, pp. 1015-1027.

Vinogradoff et a;/, Development of a New Synthesis of . . . Sodium Salt via an Amidine Intermediate, J. Heterocyclic Chem. vol. 26, 97, Jan.-Feb. 1989, pp. 97-103.

Ward, et al., "Epidermal Growth Factor Receptor Tyrosine Kinase—Investigation of Catalytic Mechanism, Structure-Based Searching and Discovery of a Potent Inhibitor," Biochem. Pharmacology, vol. 48, No. 4, pp. 659-666 (1994).

Wolfe et al., A Facile One-Step Synthesis of Certain 4-(4-Pyrimidinylmethyl)quinazolines, J. Heterocyclic Chem., vol. 13, 1976, pp. 383-385.

Hennequin et al., "ZD6474 Design, Synthesis and Structure Activity Relationship of a Novel, Orally Active VEGF Receptor Tyrosine Kinase Inhibitor," Proc. Am. Assoc. Cancer Res. 2001; 42:587, Abstract 3152.

Wedge et al., "Chronic and acute effects of ZD6474, a VEGF receptor tyrosine kinase inhibitor on established human tumor xenografts" Abstract presented at the 2000 meeting of the AACR (American Association of Cancer Research) and published in Clinical Cancer Research 2000; 6(Nov Suppl):4519S-4520S.

* cited by examiner

QUINAZOLINE DERIVATIVES AS VEGF INHIBITORS

The present invention relates to quinazoline derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Alteration of vascular permeability is thought to play a role in both normal and pathological physiological processes (Cullinan-Bove et al, 1993, Endocrinology 133: 829–837; Senger et al, 1993, Cancer and Metastasis Reviews, 12: 303–324). Several polypeptides with in vitro endothelial cell growth promoting activity have been identified-including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36:139–155) and vascular permeability (Connolly et al, 1989, J. Biol. Chem. 264: 20017–20024). Antagonism of VEGF action by sequestration of VEGF with antibody can result in inhibition of tumour growth (Kim et al, 1993, Nature 362: 841–844).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells has been associated with changes in the tyrosine phosphorylation status of cellular proteins and calcium fluxes.

Quinazoline derivatives which are inhibitors of VEGF receptor tyrosine kinase are described in International Patent Applications Publication Nos. WO 97/30035 and WO 98/13354. In WO 97/30035 and WO 98/13354 compounds are described which possess activity against VEGF receptor tyrosine kinase whilst possessing some activity against EGF receptor tyrosine kinase.

Compounds of the present invention fall within the broad general disclosure of WO 97/30035 and WO 98/13354. We have found that compounds of the present invention possess very good inhibitory activity against VEGF receptor tyrosine kinase. Compounds of the present invention, which have been tested, show in vivo activity against a range of tumour xenografts in mice. Compounds of the present invention possess a beneficial toxicological profile when tested over 14 days in rats. Compounds of the present invention possess very good inhibitory activity against VEGF receptor tyrosine kinase, show in vivo activity against a range of tumour xenografts in mice and possess a beneficial toxicological profile when tested over 14 days in rats.

Compounds of the present invention inhibit the effects of VEGF, a property of value in the treatment of disease states associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation.

Compounds of the present invention posses good activity against VEGF receptor tyrosine kinase whilst possessing some activity against EGF receptor tyrosine kinase. Furthermore, some compounds of the present invention, possess substantially higher potency against VEGF receptor tyrosine kinase than against EGF receptor tyrosine kinase or FGF R1 receptor tyrosine kinase. While we do not wish to be bound by theoretical considerations such compounds may for example be of interest in treating tumours which are associated with VEGF, especially those tumours which are dependent on VEGF for their growth. It is further believed that these compounds may be of interest in treating tumour states associated with both VEGF and EGF, especially where a patient is suffering from a condition in which tumours are present which are dependent on both VEGF and EGF for their growth.

According to one aspect of the present invention there is provided a quinazoline derivative of the formula I:

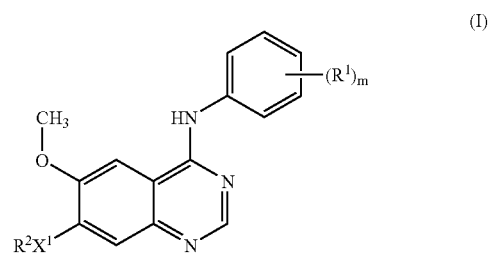

(I)

wherein:

m is an integer from 1 to 3;

$R^1$ represents halogeno or $C_{1-3}$alkyl;

$X^1$ represents —O—;

$R^2$ is selected from one of the following three groups:

1) $C_{1-5}$alkyl$R^3$ (wherein $R^3$ is piperidin-4-yl which may bear one or two substituents selected from hydroxy, halogeno, $C_{1-4}$alkyl, $C_{1-4}$hydroxyalkyl and $C_{1-4}$alkoxy;

2) $C_{2-5}$alkenyl$R^3$ (wherein $R^3$ is as defined hereinbefore);

3) $C_{2-5}$alkynyl$R^3$ (wherein $R^3$ is as defined hereinbefore);

and wherein any alkyl, alkenyl or alkynyl group may bear one or more substituents selected from hydroxy, halogeno and amino;

or a salt thereof or a prodrug thereof.

Preferably m is 2.

Preferably the phenyl group bearing $(R^1)_m$ is selected from 2-fluoro-4-methylphenyl, 4-chloro-2,6-difluorophenyl, 4-bromo-2,6-difluorophenyl, 4-chloro-2-fluorophenyl group and 4-bromo-2-fluorophenyl.

More preferably the phenyl group bearing $(R^1)_m$ is selected from 4-chloro-2-fluorophenyl and 4-bromo-2-fluorophenyl.

Most preferably the phenyl group bearing $(R^1)_m$ is 4-bromo-2-fluorophenyl.

Preferably $R^2$ is $C_{1-3}$alkyl$R^3$ (wherein $R^3$ is as defined hereinbefore).

More preferably $R^2$ is $C_{1-3}$alkyl$R^3$ (wherein $R^3$ is as defined hereinbefore).

Particularly $R^2$ is piperidin-4-ylmethyl in which the piperidine ring may bear one or two substituents as defined hereinbefore.

More particularly $R^2$ is piperidin-4-ylmethyl in which the piperidine ring may bear one or two substituents selected from $C_{1-4}$alkyl.

Especially $R^2$ is 1-methylpiperidin-4-ylmethyl.

According to a further aspect of the present invention there is provided a quinazoline derivative of the formula II:

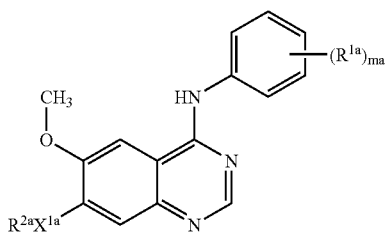

(II)

wherein:

ma is an integer from 1 to 3;

$R^{1a}$ represents halogeno or $C_{1-3}$alkyl;

$X^{1a}$ represents —O—;

$R^{2a}$ is selected from one of the following three groups:

1) $C_{1-5}$-alkyl$R^3$ (wherein $R^3$ is as defined hereinbefore);

2) $C_{2-5}$alkenyl$R^3$ (wherein $R^3$ is as defined hereinbefore);

3) $C_{2-5}$alkynyl$R^3$ (wherein $R^3$ is as defined hereinbefore);

or a salt thereof or a prodrug thereof.

Preferably ma is 2.

Preferably the phenyl group bearing $(R^{1a})_{ma}$ is selected from 2-fluoro-4-methylphenyl, 4-chloro-2,6-difluorophenyl, 4-bromo-2,6-difluorophenyl, 4-chloro-2-fluorophenyl group and 4-bromo-2-fluorophenyl.

More preferably the phenyl group bearing $(R^{1a})_{ma}$ is selected from 4-chloro-2-fluorophenyl and 4-bromo-2-fluorophenyl.

Most preferably the phenyl group bearing $(R^{1a})_{ma}$ is 4-bromo-2-fluorophenyl.

Preferably $R^{2a}$ is $C_{1-5}$alkyl$R^3$ (wherein $R^3$ is as defined hereinbefore).

More preferably $R^{2a}$ is $C_{1-3}$alkyl$R^3$ (wherein $R^3$ is as defined hereinbefore).

Particularly $R^{2a}$ is piperidin-4-ylmethyl in which the piperidine ring may bear one or two substituents as defined hereinbefore.

More particularly $R^{2a}$ is piperidin-4-ylmethyl in which the piperidine ring may bear one or two substituents selected from $C_{1-4}$alkyl.

Especially $R^{2a}$ is 1-methylpiperidin-4-ylmethyl.

Preferred compounds of the present invention include:
4-(4-chloro-2-fluoroanilino)-6-methoxy-7-(1-methylpiperidin-4-ylmethoxy)quinazoline,
4-(2-fluoro-4-methylanilino)-6-methoxy-7-(1-methylpiperidin-4-ylmethoxy)quinazoline,
4-(4-bromo-2-fluoroanilino)methoxy-7-(1-methylpiperidin-4-ylmethoxy)quinazoline,
4-(4-chloro-2,6-difluoroanilino)-6-methoxy-7-(1-methylpiperidin-4-ylmethoxy)quinazoline,
4-(4-bromo-2,6-difluoroanilino)-6-methoxy-7-(1-methylpiperidin-4-ylmethoxy)quinazoline,
4-(4-chloro-2-fluoroanilino)-6-methoxy-7-(piperidin-4-ylmethoxy)quinazoline,
4-(2-fluoro-4-methylanilino)-6-methoxy-7-(piperidin-4-ylmethoxy)quinazoline,
4-(4-bromo-2-fluoroanilino)-6-methoxy-7-(piperidin-4-ylmethoxy)quinazoline,
4-(4-chloro-2,6-difluoroanilino)-6-methoxy-7-(piperidin-4-ylmethoxy)quinazoline,
4-(4-bromo-2,6-difluoroanilino)-6-methoxy-7-(piperidin-4-ylmethoxy)quinazoline, and salts thereof especially hydrochloride salts thereof.

More preferred compounds of the present invention include:
4-(4-chloro-2-fluoroanilino)-6-methoxy-7-(1-methylpiperidin-4-ylmethoxy)quinazoline,
4-(4-bromo-2-fluoroanilino)-6-methoxy-7-(1-methylpiperidin-4-ylmethoxy)quinazoline,
4-(4-chloro-2,6-difluoroanilino)-6-methoxy-7-(methylpiperidin-4-ylmethoxy)quinazoline,
4-(4-bromo-2, difluoroanilino)-6-methoxy-7-(1-methylpiperidin-4-ylmethoxy)quinazoline,
4-(4-chloro-2-fluoroanilino)-6-methoxy-7-(piperidin-4-ylmethoxy)quinazoline,
4-(4-bromo-2-fluoroanilino)-6-methoxy-7-(piperidin-4-ylmethoxy)quinazoline,
4-(4-chloro-2,6-difluoroanilino)-6-methoxy-7-(piperidin-4-ylmethoxy)quinazoline, and
4-(4-bromo-2,6-difluoroanilino)-6-methoxy-7-(piperidin-4-ylmethoxy)quinazoline, and salts thereof especially hydrochloride salts thereof.

Particularly preferred compounds of the present invention include:

4-(4-chloro-2-fluoroanilino)-6-methoxy-7-(1-methylpiperidin-4-ylmethoxy)quinazoline, 4-(4-bromo-2-fluoroanilino)-6-methoxy-7-(1-methylpiperidin-4-ylmethoxy)quinazoline, 4-(4-chloro-2,6-difluoroanilino)-6-methoxy-7-(1-methylpiperidin-4-ylmethoxy)quinazoline, and 4-(4-bromo-2,6-difluoroanilino)-6-methoxy-7-(1-methylpiperidin-4-ylmethoxy)quinazoline, and salts thereof especially hydrochloride salts thereof.

More particularly preferred compounds of the present invention include:

4-(4-chloro-2-fluoroanilino)-6-methoxy-7-(1-methylpiperidin-4-ylmethoxy)quinazoline and 4-(4-bromo-2-fluoroanilino)-methoxy-7-(1-methylpiperidin-4-ylmethoxy)quinazoline, and salts thereof especially hydrochloride salts thereof.

An especially preferred compound of the present invention is 4-(4-bromo-2-fluoroanilino)-6-methoxy-7-(1-methylpiperidin-4-ylmethoxy)quinazoline and salts thereof especially hydrochloride salts thereof.

For the avoidance of doubt it is to be understood that where in this specification a group is qualified by 'hereinbefore defined' or 'defined hereinbefore' the said group encompasses the first occurring and broadest definition as well as each and all of the preferred definitions for that group. And a similar convention applies to 'hereinafter defined' or 'defined hereinafter'.

In this specification unless stated otherwise the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1–5 carbon atoms, preferably 1–3 carbon atoms. The term "alkoxy" as used herein, unless stated otherwise includes: "alkyl" —O— groups in which "alkyl" is as hereinbefore defined. The term "aryl" as used herein unless stated otherwise includes reference to a $C_{6-10}$ aryl group which may, if desired, carry one or more substituents selected from halogeno, alkyl, alkoxy, nitro, trifluoromethyl and cyano, (wherein alkyl and alkoxy are as hereinbefore defined). The term "aryloxy" as used herein unless otherwise stated includes "aryl" —O-groups in which "aryl" is as hereinbefore defined. The term "sulphonyloxy" as used herein refers to alkylsulphonyloxy and arylsulphonyloxy groups in which "alkyl" and "aryl" are as hereinbefore defined. The term "alkanoyl" as used herein unless otherwise stated includes formyl and alkylC=O groups in which "alkyl" is as defined hereinbefore, for example $C_2$alkanoyl is ethanoyl and refers to $CH_3C=O$, $C_1$alkanoyl is formyl and refers to CHO. In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2–5 carbon atoms, preferably 3–5 carbon atoms. In this specification unless stated otherwise the term "alkynyl" includes both straight and branched chain alkynyl groups but references to individual alkynyl groups such as 2-butenyl are specific for the straight chain version only. Unless otherwise stated the term "alkynyl" advantageously refers to chains with 2–5 carbon atoms, preferably 3–5 carbon atoms.

In formula I, as hereinbefore defined, hydrogen will be present at positions 2, 5 and 8 of the quinazoline group.

Within the present invention it is to be understood that a compound of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and is not to be limited merely to any one tautomeric form utilised within the formulae drawings.

It is also to be understood that certain compounds of the formula I and salts thereof can exist in solvated as well as unsolvated forms such as, for example, hydrated forms. It is to be understood that the invention encompasses all such solvated forms which inhibit VEGF receptor tyrosine kinase activity.

For the avoidance of any doubt, it is to be understood that in a compound of the formula I when $R^2$ is, for example, a group of formula $C_{2-5}$alkenyl$R^3$ it is the $C_{2-5}$alkenyl moiety which is bound to $X^1$ and an analogous convention applies to other groups. When $R^2$ is a group 1-$R^3$prop-1-en-3-yl it is the first carbon to which the group $R^3$ is attached and it is the third carbon which is linked to $X^1$, similarly when $R^2$ is a group 2-$R^3$pent-3-en-5-yl it is the second carbon to which the group $R^3$ is attached and it is the fifth carbon which is linked to $X^1$, and an analogous convention applies to other groups.

Compounds of Formula I may be administered in the form of a prodrug which is broken down in the human or animal body to give a compound of the Formula I. Examples of prodrugs include in vivo hydrolysable esters of a compound of the Formula I.

Various forms of prodrugs are known in the art. For examples of such prodrug derivatives see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

An in vivo hydrolysable ester of a compound of Formula I containing a hydroxy group includes inorganic esters such as phosphate esters (including phosphoramidic cyclic esters) and a-acyloxyalkyl ethers and related compounds which as a result of the in vivo hydrolysis of the ester breakdown to give the parent hydroxy groups. Examples of a-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl, (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3-or 4-position of the benzoyl ring.

The present invention relates to the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

A compound of the formula I, or salt thereof, and other compounds of the invention (as hereinafter defined) may be prepared by any process known to be applicable to the preparation of chemically-related compounds. Such processes include, for example, those illustrated in European Patent Applications, Publication Nos. 0520722, 0566226, 0602851 and 0635498 and in International Patent Applications Publication Nos. WO 97/22596, WO 97/30035, WO 97/32856 and WO 98/13354. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus the following processes (a) to (d) and (i) to (iv) constitute further features of the present invention.

Synthesis of Compounds of Formula I (a) Compounds of the formula I and salts thereof may be prepared by the reaction of a compound of the formula III:

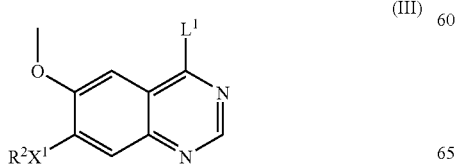

(III)

(wherein $R^2$ and $X^1$ are as defined hereinbefore and $L^1$ is a displaceable moiety), with a compound of the formula IV:

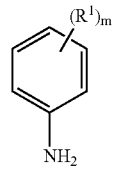

(IV)

(wherein $R^1$ and m are as defined hereinbefore) whereby to obtain compounds of the formula I and salts thereof. A convenient displaceable moiety $L^1$ is, for example, a halogeno, alkoxy (preferably $C_{1-4}$alkoxy), aryloxy or sulphonyloxy group, for example a chloro, bromo, methoxy, phenoxy, methanesulphonyloxy or toluene-4-sulphonyloxy group.

The reaction is advantageously effected in the presence of either an acid or a base. Such an acid is, for example, an anhydrous inorganic acid such as hydrogen chloride. Such a base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or for example, an alkali metal or alkaline earth metal carbonate or hydroxide, for example sodium carbonate, potassium carbonate, calcium carbonate, sodium hydroxide or potassium hydroxide. Alternatively such a base is, for example, an alkali metal hydride, for example sodium hydride, or an alkali metal or alkaline earth metal amide, for example sodium amide or sodium bis(trimethylsilyl)amide. The reaction is preferably effected in the presence of an inert solvent or diluent, for example an alkanol or ester such as methanol, ethanol, 2-propanol or ethyl acetate, a halogenated solvent such as methylene chloride, trichloromethane or carbon tetrachloride, an ether such as tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethylsulphoxide. The reaction is conveniently effected at a temperature in the range, for example, 10 to 150° C., preferably in the range 20 to 80° C.

The compound of the invention may be obtained from this process in the form of the free base or alternatively it may be obtained in the form of a salt with the acid of the formula H—$L^1$ wherein $L^1$ has the meaning defined hereinbefore. When it is desired to obtain the free base from the salt, the salt may be treated with a base as defined hereinbefore using a conventional procedure.

(b) Compounds of the formula I and salts thereof may be prepared by the reaction, conveniently in the presence of a base as defined hereinbefore, of a compound of the formula V:

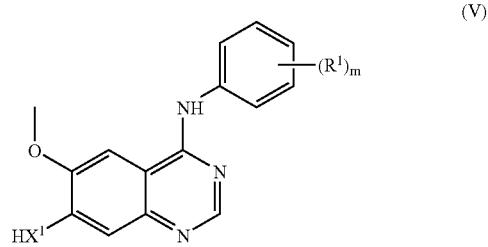

(V)

(wherein m, $X^1$ and $R^1$ are as hereinbefore defined) with a compound of formula VI:

(wherein $R^2$ and $L^1$ are as hereinbefore defined); $L^1$ is a displaceable moiety for example a halogeno or sulphonyloxy group such as a bromo or methanesulphonyloxy group. Conveniently $L^1$ is a group $O—^+P(Y)_3$ (wherein Y is butyl or phenyl) and in such cases the compound of formula VI is conveniently formed in situ. The reaction is preferably effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 50° C.

(c) Compounds of the formula I and salts thereof may be prepared by the reaction of a compound of the formula VII:

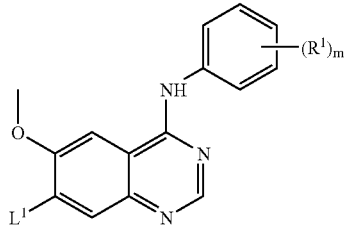

with a compound of the formula VIII:

(wherein $L^1$, $R^1$, $R^2$, m and $X^1$ are all as hereinbefore defined). The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

(d) Compounds of the formula I and salts thereof may be prepared by the deprotection of a compound of the formula IX:

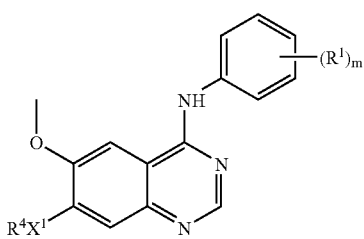

wherein $R^1$, m and $X^1$ are all as hereinbefore defined, and $R^4$ represents a protected $R^2$ group wherein $R^2$ is as defined hereinbefore but additionally bears one or more protecting groups $P^2$, The choice of protecting group $P^2$ is within the standard knowledge of an organic chemist, for example those included in standard texts such as "Protective Groups in Organic Synthesis" T. W. Greene and R. G. M. Wuts, 2nd Ed. Wiley 1991. Preferably $P^2$ is a protecting group such as a carbamate (alkoxycarbonyl) (such as, for example, tert-butoxycarbonyl, tert-amyloxycarbonyl, cyclobutoxycarbonyl, propoxycarbonyl, methoxycarbonyl, ethoxycarbonyl, isopropoxycarbonyl, allyloxycarbonyl or benzyloxycarbonyl). More preferably $P^2$ is tert-butoxycarbonyl. The reaction is preferably effected in the presence of an acid. Such an acid is, for example, an inorganic acid such as hydrogen chloride, hydrogen bromide or an organic acid such as trifluoroacetic acid, trifluoromethane sulphonic acid. The reaction may be effected in the presence of an inert solvent such as methylene chloride, trichloromethane and in the presence of a trace of water. The reaction is conveniently effected at a temperature in the range, for example, 10–100° C., preferably in the range 20–80° C.

Synthesis of Intermediates (i) The compounds of formula III and salts thereof in which $L^1$ is halogeno may for example be prepared by halogenating a compound of the formula X:

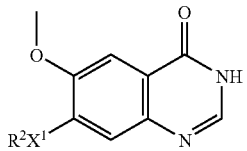

(wherein $R^2$ and $X^1$ are as hereinbefore defined).

Convenient halogenating agents include inorganic acid halides, for example thionyl chloride, phosphorus(III)chloride, phosphorus(V)oxychloride and phosphorus(V)chloride. The halogenation reaction is conveniently effected in the presence of an inert solvent or diluent such as for example a halogenated solvent such as methylene chloride, trichloromethane or carbon tetrachloride, or an aromatic hydrocarbon solvent such as benzene or toluene. The reaction is conveniently effected at a temperature in the range, for example 10 to 150° C., preferably in the range 40 to 100° C.

The compounds of formula X and salts thereof may for example be prepared by reacting a compound of the formula XI:

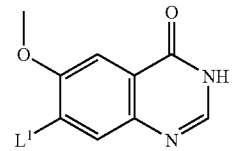

(wherein $L^1$ is as hereinbefore defined) with a compound of the formula VIII as hereinbefore defined. The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

The compounds of formula X and salts thereof may also be prepared by cyclising a compound of the formula XII:

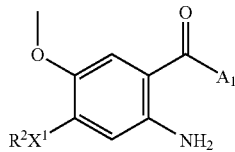

(XII)

(wherein $R^2$ and $X^1$, are as hereinbefore defined, and $A^1$ is an hydroxy, alkoxy (preferably $C_{1-4}$alkoxy) or amino group) whereby to form a compound of formula X or salt thereof. The cyclisation may be effected by reacting a compound of the formula XII, where $A^1$ is an hydroxy or alkoxy group, with formamide or an equivalent thereof effective to cause cyclisation whereby a compound of formula X or salt thereof is obtained, such as [3-(dimethylamino)-2-azaprop-2-enylidene]dimethylammonium chloride. The cyclisation is conveniently effected in the presence of formamide as solvent or in the presence of an inert solvent or diluent such as an ether for example 1,4-dioxan. The cyclisation is conveniently effected at an elevated temperature, preferably in the range 80 to 200° C. The compounds of formula X may also be prepared by cyclising a compound of the formula XII, where $A^1$ is an amino group, with formic acid or an equivalent thereof effective to cause cyclisation whereby a compound of formula X or salt thereof is obtained. Equivalents of formic acid effective to cause cyclisation include for example a tri-$C_{1-4}$alkoxymethane, for example tri-ethoxymethane and trimethoxymethane. The cyclisation is conveniently effected in the presence of a catalytic amount of an anhydrous acid, such as a sulphonic acid for example p-toluenesulphonic acid, and in the presence of an inert solvent or diluent such as for example a halogenated solvent such as methylene chloride, trichloromethane or carbon tetrachloride, an ether such as diethyl ether or tetrahydrofuran, or an aromatic hydrocarbon solvent such as toluene. The cyclisation is conveniently effected at a temperature in the range, for example 10 to 100° C., preferably in the range 20 to 50° C.

Compounds of formula XII and salts thereof may for example be prepared by the reduction of the nitro group in a compound of the formula XIII:

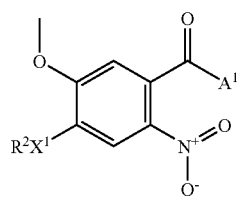

(XIII)

(wherein $R^2$, $X^1$ and $A^1$ are as hereinbefore defined) to yield a compound of formula XIII as hereinbefore defined. The reduction of the nitro group may conveniently be effected by any of the procedures known for such a transformation. The reduction may be carried out, for example, by the hydrogenation of a solution of the nitro compound in the presence of an inert solvent or diluent as defined hereinbefore in the presence of a metal effective to catalyse hydrogenation reactions such as palladium or platinum. A further reducing agent is, for example, an activated metal such as activated iron (produced for example by washing iron powder with a dilute solution of an acid such as hydrochloric acid). Thus, for example, the reduction may be effected by heating the nitro compound and the activated metal in the presence of a solvent or diluent such as a mixture of water and alcohol, for example methanol or ethanol, to a temperature in the range, for example 50 to 150° C., conveniently at about 70° C.

Compounds of the formula XIII and salts thereof may for example be prepared by the reaction of a compound of the formula XIV:

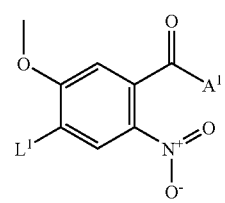

(XIV)

(wherein $L^1$ and $A^1$ are as hereinbefore defined) with a compound of the formula VIII as hereinbefore defined to give a compound of the formual XIII. The reaction of the compounds of formulae XIV and VIII is conveniently effected under conditions as described for process (c) hereinbefore.

Compounds of formula XIII and salts thereof, may for example also be prepared by the reaction of a compound of the formula XV:

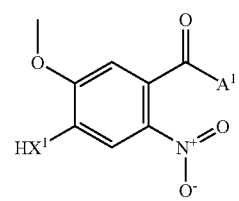

(XV)

(wherein $X^1$ and $A^1$ are as hereinbefore defined) with a compound of the formula VI as hereinbefore defined to yield a compound of formula XIII as hereinbefore defined. The reaction of the compounds of formulae XV and VI is conveniently effected under conditions as described for process (b) hereinbefore.

The compounds of formula III and salts thereof may also be prepared for example by reacting a compound of the formula XVI:

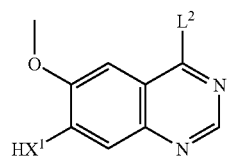

(XVI)

(wherein $X^1$ is as hereinbefore defined and $L^2$ represents a displaceable protecting moiety) with a compound of the formula VI as hereinbefore defined, whereby to obtain a compound of formula III in which $L^1$ is represented by $L^2$.

A compound of formula XVI is conveniently used in which L² represents a phenoxy group which may if desired carry up to 5 substituents, preferably up to 2 substituents, selected from halogeno, nitro and cyano. The reaction may be conveniently effected under conditions as described for process (b) hereinbefore.

The compounds of formula XVI and salts thereof as hereinbefore defined may for example be prepared by deprotecting a compound of the formula XVII:

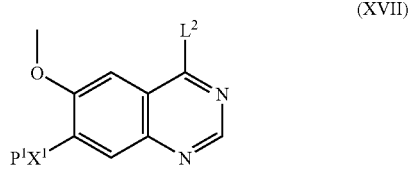

(XVII)

(wherein X¹ and L² are as hereinbefore defined and P¹ represents a phenolic hydroxy protecting group). The choice of phenolic hydroxy protecting group P¹ is within the standard knowledge of an organic chemist, for example those included in standard texts such as "Protective Groups in Organic Synthesis" T. W. Greene and R. G. M. Wuts, 2nd Ed. Wiley 1991, including ethers (for example, methyl, methoxymethyl, allyl and benzyl and benzyl substituted with up to two substituents selected from C₁₋₄alkoxy and nitro), silyl ethers (for example, t-butyldiphenylsilyl and t-butyldimethylsilyl), esters (for example, acetate and benzoate) and carbonates (for example, methyl and benzyl and benzyl substituted with up to two substituents selected from C₁₋₄alkoxy and nitro). Deprotection may be effected by techniques well known in the literature, for example where P¹ represents a benzyl group deprotection may be effected by hydrogenolysis or by treatment with trifluoroacetic acid.

The removal of such a phenolic hydroxy protecting group may be effected by any of the procedures known for such a transformation, including those reaction conditions indicated in standard texts such as that indicated hereinbefore, or by a related procedure. The reaction conditions preferably being such that the hydroxy derivative is produced without unwanted reactions at other sites within the starting or product compounds. For example, where the protecting group P¹ is acetate, the transformation may conveniently be effected by treatment of the quinazoline derivative with a base as defined hereinbefore and including ammonia, and its mono and di-alkylated derivatives, preferably in the presence of a protic solvent or co-solvent such as water or an alcohol, for example methanol or ethanol. Such a reaction can be effected in the presence of an additional inert solvent or diluent as defined hereinbefore and at a temperature in the range 0 to 50° C., conveniently at about 20° C.

One compound of formula III may if desired be converted into another compound of formula III in which the moiety L¹ is different. Thus for example a compound of formula III in which L¹ is other than halogeno, for example optionally substituted phenoxy, may be converted to a compound of formula III in which L¹ is halogeno by hydrolysis of a compound of formula III (in which L¹ is other than halogeno) to yield a compound of formula X as hereinbefore defined, followed by introduction of halide to the compound of formula X thus obtained as hereinbefore defined, to yield a compound of formula III in which L¹ represents halogeno.

(ii) Compounds of the formula V as hereinbefore defined and salts thereof may be made by deprotecting the compound of formula XVIII:

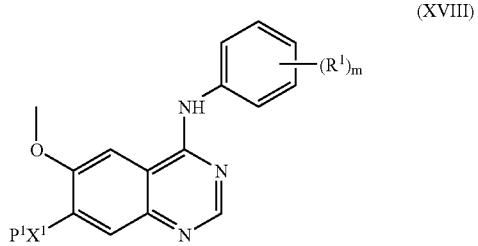

(XVIII)

(wherein R¹, P¹, X¹ and m are as hereinbefore defined) by a process for example as described in (i) above.

Compounds of the formula XVIII and salts thereof may be made by reacting compounds of the formula XVII and IV as hereinbefore defined, under the conditions described in (a) hereinbefore, to give a compound of the formula XVIII or salt thereof.

(iii) Compounds of the formula VII and salts thereof as hereinbefore defined may be made by reacting a compound of the formula XIX:

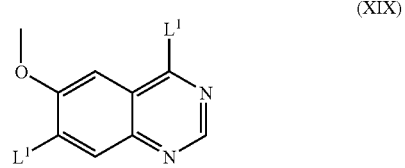

(XIX)

(wherein L¹ is as hereinbefore defined, and L¹ in the 4- and 7-positions may be the same or different) with a compound of formual IV as hereinbefore defined, the reaction for example being effected by a process as described in (a) above.

(iv) A compound of the formula IX may be prepared by the reaction of a compound of the formula V as defined hereinbefore with a compound of the formula XX:

R⁴—L¹                     (XX)

wherein R⁴ and L¹ are as defined hereinbefore under the conditions described in (b) hereinbefore to give a compound of the formula IX or salt thereof. The reaction is preferably effected in the presence of a base (as defined hereinbefore in process (a)) and advantageously in the presence of an inert solvent or diluent (as defined hereinbefore in process (a)), advantageously at a temperature in the range, for example 10 to 150° C., conveniently in the range 20–50° C.

When a pharmaceutically acceptable salt of a compound of the formula I is required, it may be obtained, for example, by reaction of said compound with, for example, an acid using a conventional procedure, the acid having a pharmaceutically acceptable anion, or it may be obtained by reaction of said compound with a base by a conventional procedure.

The identification of compounds which potently inhibit the tyrosine kinase activity associated with the VEGF receptors such as Flt and/or KDR and which inhibit angiogenesis and/or increased vascular permeability is desirable and is the subject of the present invention. These properties may be assessed, for example, using one or more of the procedures set out below:

(a) In Vitro Receptor Tyrosine Kinase Inhibition Test

This assay determines the ability of a test compound to inhibit tyrosine kinase activity. DNA encoding VEGF or epidermal growth factor (EGF) receptor cytoplasmic domains may be obtained by total gene synthesis (Edwards M, International Biotechnology Lab 5(3), 19–25, 1987) or by cloning. These may then be expressed in a suitable expression system to obtain polypeptide with tyrosine kinase activity. For example VEGF and EGF receptor cytoplasmic domains, which were obtained by expression of recombinant protein in insect cells, were found to display intrinsic tyrosine kinase activity. In the case of the VEGF receptor Flt (Genbank accession number X51602), a 1.7 kb DNA fragment encoding most of the cytoplasmic domain, commencing with methionine 783 and including the termination codon, described by Shibuya et al (Oncogene, 1990, 5: 519–524), was isolated from cDNA and cloned into a baculovirus transplacement vector (for example pAcYM1 (see The Baculovirus Expression System: A Laboratory Guide, L. A. King and R D. Possee, Chapman and Hall, 1992) or pAc360 or pBlueBacHis (available from Invitrogen Corporation)). This recombinant construct was co-transfected into insect cells (for example *Spodoptera frugiperda* 21(Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning— A Laboratory Manual, 2nd edition, Cold Spring Harbour Laboratory Press and O'Reilly et al, 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947) and methionine 668 (EGF receptor, Genbank accession number X00588) may be cloned and expressed in a similar manner.

For expression of cFlt tyrosine kinase activity, Sf21 cells were infected with plaque-pure cFlt recombinant virus at a multiplicity of infection of 3 and harvested 48 hours later. Harvested cells were washed with ice cold phosphate buffered saline solution (PBS) (10 mM sodium phosphate pH 7.4, 138 mM sodium chloride, 2.7 mM potassium chloride) then resuspended in ice cold HNTG/PMSF (20 mM Hepes pH 7.5, 150 mM sodium chloride, 10% v/v glycerol, 1% v/v Triton X100, 1.5 mM magnesium chloride, 1 mM ethylene glycol-bis(βaminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM sodium orthovanadate, 0.1% v/v Triton X100, 0.2 mM dithiothreitol). For a typical batch, stock enzyme is diluted 1 in 2000 with enzyme diluent and 50 µl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100µ of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH 7.4.

Test compounds were diluted with 10% dimethylsulphoxide (DMSO) and 25 µl of diluted compound was transferred to wells in the washed assay plates. "Total" control wells contained 10% DMSO instead of compound. Twenty five microliters of 40 mM manganese(II)chloride containing 8 µM adenosine-5'-triphosphate (ATP) was added to all test wells except "blank" control wells which contained manganese(II)chloride without ATP. To start the reactions 50 µl of freshly diluted enzyme was added to each well and the plates were incubated at room temperature for 20 minutes. The liquid was then discarded and the wells were washed twice with PBST. One hundred microliters of mouse IgG anti-phosphotyrosine antibody (Upstate Biotechnology Inc. product 05-321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microliters of horse radish peroxidase (HRP)-linked sheep anti-mouse Ig antibody (Amersham product NXA 931), diluted 1 in 500 with PBST containing 0.5% wiv BSA, was added and the plates were incubated for 1 hour at room temperature before discarding the liquid and washing the wells twice with PBST. One hundred microliters of 2,2'-azino-bis(3-ethyl-benzthiazoline-6-sulphonic acid) (ABTS) solution, freshly prepared using one 50 mg ABTS tablet (Boehringer 1204 521) in 50 ml freshly prepared 50 mM phosphate-citrate buffer pH 5.0+0.03% sodium perborate (made with 1 phosphate citrate buffer with sodium perborate (PCSB) capsule (Sigma P4922) per 100 ml distilled water), was added to each well. Plates were then incubated for 2040 minutes at room temperature until the optical density value: of the "total" control wells, measured at 405 nm using a plate reading spectrophotometer, was approximately 1.0. "Blank" (no ATP) and "total" (no compound) control values were used to determine the dilution range of test compound which gave 50% inhibtion of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+ 7.5% v/v foetal calf serum (FCS) and were plated out (at passage 2 to 8), in MCDB 131+2% v/v FCS+3 µg/ml heparin +1 µg/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% carbon dioxide. On day 4 the cultures were pulsed with 1 µCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In Vivo Solid Tumour Disease Model

This test measures the capacity of compounds to inhibit solid tumour growth.

CaLu-6 tumour xenografts were established in the flank of female athymic Swiss nu/nu mice, by subcutaneous injection of $1\times10^6$ CaLu-6 cells/mouse in 100 µl of a 50% (v/v) solution of Matrigel in serum free culture medium. Ten days after cellular implant, mice were allocated to groups of 8–10, so as to achieve comparable group mean volumes. Tumours were measured using vernier calipers and volumes were calculated as: $(l\times w)\times\sqrt{(l\times w)}\times(\pi/6)$, where 1 is the longest diameter and w the diameter perpendicular to the longest diameter. Test compounds were administered orally once daily for a minimum of 21 days, and control animals received compound diluent. Tumours were measured twice weekly. The level of growth inhibition was calculated by comparison of the mean tumour volume of the control group versus the treatment group, and statistical significance determined using a Students' t-test and/or a Mann-Whitney Rank Sum Test. The inhibitory effect of compound treatment was considered significant when $p<0.05$.

The toxicological profile of compounds of the present invention may be assessed, for example using a rat 14 day study as described hereinafter.

(d) 14 Day Toxicity Test in Rat

This test measures the activity of compounds in increasing the zone of hypertrophy in the femoral epiphyseal growth plates of the distal femur and proximal tibia, and allows assessment of histopathological changes in other tissues.

Angiogenesis is an essential event in endochondral ossification during long bone elongation, and vascular invasion of the growth plate has been suggested to depend upon VEGF production by hypertrophic chondrocytes. Expansion of the hypertrophic chondrocyte zone and inhibition of angiogenesis has been demonstrated following treatment with agents which specifically sequester VEGF, such as, for example, (i) a soluble VEGF receptor chimeric protein (Flt-(1-3)-IgG) in mice (Gerber, H.-P., Vu, T. H., Ryan, A. M., Kowalski, J., Werb, Z. and Ferrara; N. VEGF couples hypertrophic cartilage remodelling, ossification and angiogenesis during endochondral bone formation, Nature Med., 5: 623–628, 1999) and (ii) a recombinant humanised anti-VEGF monoclonal IgG1 antibody in cynomologus monkey (Ryan, A. M., Eppler, D. B., Hagler, K. E., Bruner, R. H., Thomford, P. J., Hall, R. L., Shopp, G. M. and O'Niell, C. A. Preclinical Safety Evaluation of rhuMAbVEGF, an anti-angiogenic humanised monoclonal antibody, Tox. Path., 27: 78–86, 1999).

An inhibitor of VEGF receptor tyrosine kinase activity should therefore also inhibit vascular invasion of cartilage, and increase the zone of hypertrophy in the femoral epiphyseal growth plates of the distal femur and proximal tibia in growing animals.

Compounds were initially formulated by suspension in a 1% (v/v) solution of polyoxyethylene (20) sorbitan monooleate in deionised water, by ball-milling at 4° C. overnight (at least 15 hours). Compounds were re-suspended by agitation immediately prior to dosing. Young Alderley Park rats (Wistar derived, 135–150 g in weight, 4 to 8 weeks of age, 5–6 per group) were dosed once-daily by oral gavage for 14 consecutive days with compound (at 0.25 ml/100 g body weight) or vehicle. On day 15 animals were humanely terminated using a rising concentration of carbon dioxide, and a post-mortem performed. A range of tissues, which included femoro-tibial joints, were collected and processed by standard histological techniques to produce paraffin wax sections. Histological sections were stained with haematoxylin and eosin and examined by light microscopy for histopathology. The femoral epiphyseal growth plate areas of the distal femur and proximal tibia were measured in sections of femur and tibia using morphometric image analysis. The increase in the zone of hypertrophy was determined by comparison of the mean epiphyseal growth plate area of the control group versus the treatment group, and statistical significance determined using a one-tailed Students' t-test. The inhibitory effect of compound treatment was considered significant when $p<0.05$.

Although the pharmacological properties of the compounds of Formula I vary with structural change, in general, activity possessed by compounds of the Formula I, may be demonstrated at the following concentrations or doses in one or more of the above tests (a), (b), (c) and (d):

Test (a):—$IC_{50}$ in the range, for example, <5 µM;
Test (b):—$IC_{50}$ in the range, for example, 0.001–5 µM;
Test (c):—activity in the range, for example, 0.1–100 mg/kg;
Test (d):—activity in the range, for example, 0.1–100 mg/kg.

According to one aspect of the present invention compounds of Formula I, assessed in the 14 day toxicity test in rat, have a beneficial toxicological profile over other compounds within the scope of International Patent Application Publication No. WO 98/13354.

According to another aspect of the present invention compounds of Formula I, assessed in the 14 day toxicity test in rat, have a beneficial toxicological profile over other compounds within the scope of International Patent Application Publication No. WO 97/30035.

Although the pharmacological properties of the compounds of Formula I vary with structural change and between species, at doses in the rat, preferably at doses less than or equal to 150 mg/kg, more preferably at doses less than or equal to 100 mg/kg, especially at doses less than or equal to 50 mg/kg, compounds of Formula I which produce a statistically significant increase in the femoral epiphyseal growth plate area of the distal femur and/or proximal tibia, produce no unacceptable histopathological changes in other tissues in tests (d) that we have conducted.

Thus by way of example, the compound 4-(4-bromo-2-fluoroanilino)-6-methoxy-7-(1-methylpiperidin-4-yl-methoxy)quinazoline, (Example 2), tested according to (a), (b), (c) and (d) above gave the following results:

(a) Flt—$IC_{50}$ of 1.6 µM
KDR—$IC_{50}$ of 0.04 µM
EGFR—$IC_{50}$ of 0.5 µM (b) VEGF—$IC_{50}$ of 0.06 µM
EGF—$IC_{50}$ of 0.17 µM
Basal—$IC_{50}$ of >3 µM (c) 78% inhibition of tumour growth at 50 mg/kg; $p<0.001$ (Mann-Whitney Rank Sum Test);

(d) 75% increase in epiphyseal growth plate hypertrophy at 100 mg/kg/day in female rats; $p<0.001$ (one-tailed Students' t-test).

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, (for example as tablets, lozenges, hard or soft capsules, aqueous or oily suspensions, emulsions, dispersible powders or granules, syrups or elixirs), for administration by inhalation (for example as a finely divided powder or a liquid aerosol), for administration by insufflation (for example as a finely divided powder), for parenteral injection (for example as a sterile solution, suspension or emulsion for intravenous, subcutaneous, intramuscular, intravascular or infusion dosing), for topical administration (for example as creams, ointments, gels, or aqueous or oily solutions or suspensions), or for rectal administration (for example as a suppository). In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square meter body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and are therefore of interest for their antiangiogenic effects and/or their ability to cause a reduction in vascular permeability.

A further feature of the present invention is a compound of formula I, or a pharmaceutically acceptable salt thereof, for use as a medicament, conveniently a compound of formula I, or a pharmaceutically acceptable salt thereof, for use as a medicament for producing an antiangiogenic and/or vascular permeability reducing effect in a warm-blooded animal such as a human being.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be surgery, radiotherapy or chemotherapy. Such chemotherapy may cover five main categories of therapeutic agent:

(i) other antiangiogenic agents that work by different mechanisms from those defined hereinbefore (for example linomide, inhibitors of integrin $\alpha v\beta 3$ function, angiostatin, endostatin, razoxin, thalidomide) and including vascular targeting agents (for example combretastatin phosphate and the vascular damaging agents described in International Patent Application Publication No. WO 99/02166 the entire disclosure of which document is incorporated herein by reference, (for example N-acetylcolchinol-O-phosphate));

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide, abarelix), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors);

(iii) biological response modifiers (for example interferon);

(iv) antibodies (for example edrecolomab); and (v) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); enzymes (for example asparaginase); thymidylate synthase inhibitors (for example raltitrexed); topoisomerase inhibitors (for example epipodophyllotoxins like etoposide and teniposide, amsacrine, topotecan, irinotecan).

For example such conjoint treatment may be achieved by way of the simultaneous, sequential or separate administration of a compound of formula I as defined hereinbefore such as 4-(4-bromo-2-fluoroanilino)-6-methoxy-7-(1-methylpiperidin-4-ylmethoxy)quinazoline or a salt thereof especially a hydrochloride salt thereof, and a vascular targeting agent described in WO 99/02166 such as N-acetylcolchinol-O-phosphate (Exampe 1 of WO 99/02166).

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, acute and chronic nephropathies, atheroma, arterial-restenosis, autoimmune diseases, acute inflammation, excessive scar formation and adhesions, endometriosis, dysfunctional uterine bleeding and ocular diseases with retinal vessel proliferation. In particular such compounds of the invention are expected to slow advantageously the growth of primary and recurrent solid tumours of, for example, the colon, breast, prostate, lungs and skin. More particularly such compounds of the invention are expected to inhibit the growth of those primary and recurrent solid tumours which are associated with VEGF especially those tumours which are significantly dependent on VEGF for their growth and spread, including for example, certain tumours of the colon, breast, prostate, lung, vulva and skin.

In another aspect of the present invention compounds of Formula I are expected to inhibit the growth of those primary and recurrent solid tumours which are associated with EGF especially those tumours which are significantly dependent on EGF for their growth and spread.

In another aspect of the present invention compounds of Formula I are expected to inhibit the growth of those primary and recurrent solid tumours which are associated with both VEGF and EGF especially those tumours which are significantly dependent on VEGF and EGF for their growth and spread.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated, but not limited, by the following Examples in which, unless otherwise stated:—

(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet; NMR spectra were run on a 400 MHz machine at 24° C.

(vii) intermediates were not generally fully characterised and purity was assessed by thin layer chromatography (TLC), high-performance liquid chromatography (HPLC), infra-red (IR) or NMR analysis;

(viii) the following abbreviations have been used:—
DMF N,N-dimethylformamide
DMSO dimethylsulphoxide
THF tetrahydrofuran
TFA trifluoroacetic acid
NMP 1-methyl-2-pyrrolidinone.]

EXAMPLE 1

TFA (3 ml) was added to a suspension of 4-(4-bromo-2-fluoroanilino)-7-(1-(tert-butoxycarbonyl)piperidin-4-ylmethoxy)-6-methoxyquinazoline (673 mg, 1.2 mmol) in methylene chloride (10 ml). After stirring for 1 hour at ambient temperature, the volatiles were removed under vacuum. The residue was triturated with a mixture of water/ether. The organic layer was separated. The aqueous layer was washed again with ether. The aqueous layer was adjusted to pH 10 with 2N aqueous sodium hydroxide. The aqueous layer was extracted with methylene chloride. The organic layer was dried ($MgSO_4$) and the solvent was removed under vacuum. The solid was triturated with a mixture ether/petroleum ether (1/1), filtered, washed with ether and dried under vacuum to give 4-(4-bromo-2-fluoroanilino)-6-methoxy-7-(piperidin-4-ylmethoxy)quinazoline (390 mg, 70.5%).

MS—ESI: 461–463 $[MH]^+$ $^1$H NMR Spectrum: ($DMSOd_6$) 1.13–1.3 (m, 2H), 1.75 (d, 2H), 1.87–2.0 (m, 1H), 2.5 (d, 2H), 3.0 (d, 2H), 3.96 (s, 3H), 3.98 (d, 2H), 7.2 (s, 1H), 7.5 (dd, 1H), 7.55 (t, 1H), 7.68 (dd, 1H), 7.80 (s, 1H), 8.36 (s, 1H), 9.55 (br s, 1H)

Elemental analysis: $C_{21}H_{22}N_4O_2BrF$; Found C 54.5, H 4.9, N 12.1; Requires C 54.7, H 4.8, N 12.1%.

The starting material was prepared as follows:

A solution of 7-benzyloxy-4-chloro-6-methoxyquinazoline hydrochloride (8.35 g, 27.8 mmol), (prepared, for example, as described in WO 97/22596, Example 1), and 4-bromo-2-fluoroaniline (5.65 g, 29.7 mmol) in 2-propanol (200 ml) was heated at reflux for 4 hours. The resulting precipitate was collected by filtration, washed with 2-propanol and then ether and dried under vacuum to give 7-benzyloxy-4-(4-bromo-2-fluoroanilino)-6-methoxyquinazoline hydrochloride (9.46 g, 78%).

$^1$H NMR Spectrum: $DMSOd_6$; $CD_3COOD$) 4.0(s, 3H); 5.37(s, 2H); 7.35–7.5(m, 4H); 7.52–7.62(m, 4H); 7.8(d, 1H); 8.14(9s, 1H); 8.79(s, 1H) MS-ESI: 456 $[MH]^+$ Elemental analysis: $C_{22}H_{17}N_3O_2BrF$ 0.9 HCl; Found C 54.0, H 3.7, N 8.7; Requires C 54.2, H 3.7, N 8.6%.

A solution of 7-benzyloxy-4-(4-bromo-2-fluoroanilino)-6-methoxyquinazoline hydrochloride (9.4 g, 19.1 mmol) in TFA (90 ml) was heated at reflux for 50 minutes. The mixture was allowed to cool and was poured on to ice. The resulting precipitate was collected by filtration and dissolved in methanol (70 ml). The solution was adjusted to pH 9–10 with concentrated aqueous ammonia solution. The mixture was concentrated to half initial volume by evaporation. The resulting precipitate was collected by filtration, washed with water and then ether, and dried under vacuum to give 4-(4-bromo-2-fluoroanilino)-7-hydroxy-6-methoxyquinazoline (5.66 g, 82%).

$^1$H NMR Spectrum: ($DMSOd_6$; $CD_3COOD$) 3.95(s, 3H); 7.09(s, 1H); 7.48(s, 1H); 7.54(t, 1H); 7.64(d, 1H); 7.79(s, 1H); 8.31(s, 1H) MS-ESI. 366 $[MH]^+$ Elemental analysis: $C_{15}H_{11}N_3O_2BrF$; Found C 49.5, H 3.1, N 11.3; Requires C 49.5, H 3.0, N 11.5%.

While maintaining the temperature in the range 0–5° C., a solution of di-tert-butyl dicarbonate (41.7 g, 0.19 mol) in ethyl acetate (75 ml) was added in portions to a solution of ethyl 4-piperidinecarboxylate (30 g, 0.19 mol) in ethyl acetate (150 ml) cooled at 5° C. After stirring for 48 hours at ambient temperature, the mixture was poured onto water (300 ml). The organic layer was separated, washed successively with water (200 ml), 0.1N aqueous hydrochloric acid (200 ml), saturated sodium hydrogen carbonate (200 ml) and brine (200 ml), dried (MgSO$_4$) and evaporated to give ethyl 4-(1-(tert-butoxycarbonyl)piperidine)carboxylate (48 g, 98%).

$^1$H NMR Spectrum: (CDCl$_3$) 1.25(t, 3H); 1.45(s, 9H); 1.55–1.70(m, 2H); 1.8–2.0(d, 2H); 2.35–2.5(m, 1H); 2.7–2.95(t, 2H); 3.9–4.1(br s, 2H); 4.15 (q, 2H)

A solution of 1M lithium aluminium hydride in THF (133 ml, 0.133 mol) was added in portions to a solution of ethyl 4-(1-(tert-butoxycarbonyl)piperidine)carboxylate (48 g, 0.19 mol) in dry THF (180 ml) cooled at 0° C. After stirring at 0° C. for 2 hours, water (30 ml) was added followed by 2N sodium hydroxide (10 ml). The precipitate was removed by filtration through diatomaceous earth and washed with ethyl acetate. The filtrate was washed with water, brine, dried (MgSO$_4$) and evaporated to give 1-(tert-butoxycarbonyl)-4-hydroxymethylpiperidine (36.3 g, 89%).

MS (EI): 215 [M.]$^+$ $^1$H NMR Spectrum: (CDCl$_3$) 1.05–1.2(m, 2H); 0.35–1.55 (m, 10H); 1.6–1.8(m, 2H); 2.6–2.8(t, 2H); 3.4–3.6(t, 2H); 4.0–4.2(br s, 2H)

1,4-Diazabicyclo[2.2.2]octane (42.4 g, 0.378 mol) was added to a solution of 1-(tert-butoxycarbonyl)-4-hydroxymethylpiperidine (52.5 g, 0.244 mol) in tert-butyl methyl ether (525 ml). After stirring for 15 minutes at ambient temperature, the mixture was cooled to 5° C. and a solution of toluene sulphonyl chloride (62.8 g, 0.33 mmol) in tert-butyl methyl ether (525 ml) was added in portions over 2 hours while maintaining the temperature at 0° C. After stirring for 1 hour at ambient temperature, petroleum ether (1 l) was added. The precipitate was removed by filtration. The filtrate was evaporated to give a solid. The solid was dissolved in ether and washed successively with 0.5N aqueous hydrochloric acid (2×500 ml), water, saturated sodium hydrogen carbonate and brine, dried (MgSO$_4$) and evaporated to give 1-(tert-butoxycarbonyl)-4-(4-methylphenylsulphonyloxymethyl)piperidine (76.7 g, 85%).

MS (ESI): 392 [MNa]$^+$ $^1$H NMR Spectrum: (CDCl$_3$) 1.0–1.2(m, 2H); 1.45(s, 9H); 1.65(d, 2H); 1.75–1.9(m, 2H); 2.45(s, 3H); 2.55–2.75 (m, 2H); 3.85(d, 1H); 4.0–4.2(br s, 2H); 7.35(d, 2H); 7.8(d, 2H)

Potassium carbonate (414 mg, 3 mmol) was added to a suspension of 4-(4-bromo-2-fluoroanilino)-7-hydroxy-6-methoxyquinazoline (546 mg, 1.5 mmol) in DMF (5 ml). After stirring for 10 minutes at ambient temperature, 1-(tert-butoxycarbonyl)-4-(4-methylphenylsulphonyloxymethyl) piperidine (636 mg, 1.72 mmol) was added and the mixture was heated at 95° C. for 2 hours. After cooling, the mixture was poured onto cooled water (20 ml). The precipitate was collected by filtration, washed with water, and dried under vacuum to give 4-(4-bromo-2-fluoroanilino)-7-(1-(tert-butoxycarbonyl)piperidin-4-ylmethoxy)-6-methoxyquinazoline (665 mg, 79%).

MS—ESI: 561–563 [MH]$^+$ $^1$H NMR Spectrum: (DMSOd$_6$) 1.15–1.3 (m, 2H), 1.46 (s, 9H), 1.8 (d, 2H), 2.0–2.1 (m, 1H), 2.65–2.9 (m, 2H), 3.95 (s, 3H), 4.02 (br s, 2H), 4.05 (d, 2H), 7.2 (s, 1H), 7.48 (d, 1H), 7.55 (t, 1H), 7.65 (d, 1H), 7.8 (s, 1H), 8.35 (s, 1H), 9.55 (br s, 1H)

EXAMPLE 2a

A solution of 37% aqueous formaldehyde (50 μl, 0.6 mmol) followed by sodium cyanoborohydride (23 mg, 0.36 mmol) were added to a solution of 4-(4-bromo-2-fluoroanilino)-6-methoxy-7-(piperidin-4-ylmethoxy)quinazoline (139 mg, 0.3 mmol), (prepared as described in Example 1), in a mixture of THF/methanol (1.4 ml/1.4 ml). After stirring for 1 hour at ambient temperature, water was added and the volatiles were removed under vacuum. The residue was triturated with water, filtered, washed with water, and dried under vacuum. The solid was purified by chromatography on neutral alumina eluting with methylene chloride followed by methylene chloride/ethyl acetate (1/1) followed by methylene chloride/ethyl acetate/methanol (50/45/5). The fractions containing the expected product were evaporated under vacuum. The resulting white solid was dissolved in methylene chloride/methanol (3 ml/3 ml) and 3N hydrogen chloride in ether (0.5 ml) was added. The volatiles were removed under vacuum. The solid was triturated with ether, filtered, washed with ether and dried under vacuum to give 4-(4-bromo-2-fluoroanilino)-6-methoxy-7-(1-methylpiperidin-4-ylmethoxy)quinazoline hydrochloride (120 mg, 69%).

MS—ESI: 475–477 [MH]$^+$

The NMR spectrum of the protonated form of 4-(4-bromo-2-fluoroanilino-6-methoxy-7-(1-methylpiperidin-4-ylmethoxy)quinazoline hydrochloride shows the presence of 2 forms A and B in a ratio A:B of approximately 9:1.

$^1$H NMR Spectrum: (DMSOd$_6$; CF$_3$COOD) 1.55–1.7 (m, form A 2H); 1.85–2.0 (m, form B 4H); 2.03 (d, form A 2H); 2.08–2.14 (br s, form A 1H); 2.31–2.38 (br s, form B 1H); 2.79 (s, form A 3H); 2.82 (s, form B 3H); 3.03 (t, form A 2H); 3.21 (br s, form B 2H); 3.30 (br s, form B 2H); 3.52 (d, form A 2H); 4.02 (s, 3H); 4.12 (d, form A 2H); 4.30 (d, form B 2H); 7.41 (s, 1H); 7.5–7.65 (m, 2H); 7.81 (d, 1H); 8.20 (s, 1H); 8.88 (s, 1H)

Elemental analysis: C$_{23}$H$_{24}$N$_4$O$_2$BrF 0.3H$_2$O 2.65 HCl; Found C 46.0, H 5.2, N 9.6; Requires C 45.8, H 4.8, N 9.7%.

EXAMPLE 2b

37% Aqueous formaldehyde (3.5 ml, 42 mmol) was added to a solution of 4-(4-bromo-2-fluoroanilino)-7-(1-(tert-butoxycarbonyl)piperidin-4-ylmethoxy)-6-methoxyquinazoline (3.49 g, 6.22 mmol), (prepared as described for the starting material in Example 1), in formic acid (35 ml). After heating at 95° C. for 4 hours the volatiles were removed under vacuum. The residue was suspended in water and the mixture was adjusted to pH 10.5 by slow addition of a solution of 2N sodium hydroxide. The suspension was extracted with ethyl acetate. The organic layer was washed with brine, dried MgSO$_4$ and evaporated to give 4-(4-bromo-2-fluoroanilino)-6-methoxy-7-(1-methylpiperidin-4-ylmethoxy)quinazoline (2.61 g, 88%).

MS—ESI: 475–477 [MH]$^+$ $^1$H NMR Spectrum: (DMSOd$_6$) 1.3–1.45 (m, 2H), 1.8 (d, 2H), 1.7–1.9 (m, 1H), 1.95 (t, 2H), 2.2 (s, 3H), 2.85 (d, 2H), 3.96 (s, 3H), 4.05 (d, 2H), 7.19 (s, 1H), 7.5 (d, 1H), 7.55 (t, 1H), 7.67 (d, 1H), 7.81 (s, 1H), 8.37 (s, 1H), 9.54 (s, 1H)

Elemental analysis: C$_{22}$H$_{24}$N$_4$O$_2$BrF; Found C 55.4, H 5.1, N 11.6; Requires C 55.6, H 5.1, N 11.8%.

EXAMPLE 2c

A suspension of 4-chloro-6-methoxy-7-(1-methylpiperidin-4-ylmethoxy)quinazoline (200 mg, 0.62 mmol) and 4-bromo-2-fluroaniline-(142 mg; 0.74 mmol) in isopropanol (3 ml) containing 6N hydrogen chloride in isopropanol (110 μl, 0.68 ml) was heated at reflux for 1.5 hours. After cooling, the precipitate was collected by filtration, washed with isopropanol followed by ether and dried under vacuum to give 4-(4-bromo-2-fluoroanilino)-6-methoxy-7-(1-methylpiperidin-4-ylmethoxy)quinazoline hydrochloride (304 mg, 90%).

Elemental analysis: $C_{22}H_{24}N_4O_2BrF$ 0.5 $H_2O$ 1.8 HCl; Found C 47.9, H 4.9, N 10.0; Requires C 48.2, H 5.0, N 10.1%.

The NMR spectrum of the protonated form of 4-(4-bromo-2-fluoroanilino)-6-methoxy-7-(1-methylpiperidin-4-ylmethoxy)quinazoline hydrochloride shows the presence of two forms A and B in a ratio A:B of approximately 9:1.

$^1$H NMR Spectrum: ($DMSOd_6$) 1.6–1.78 (m, form A 2H); 1.81–1.93 (br s, form B 4H); 1.94–2.07 (d, form A 2H); 2.08–2.23 (br s, form A 1H); 2.29–2.37 (br s, form B 1H); 2.73 (d, form A 3H); 2.77 (d, form B 3H); 2.93–3.10 (q, form A 2H); 3.21 (br s, form B 2H); 3.27 (d, form B 2H); 3.42–3.48 (d, form A 2H); 4.04 (s, 3H); 4.10 (d, form A 2H); 4.29 (d, form B 2H); 7.49 (s, 1H); 7.53–7.61 (m, 2H); 7.78 (d, 1H); 8.47 (s, 1H); 8.81 (s, 1H); 10.48 (br s, form A 1H); 10.79 (br s, form B 1H); 11.90 (br s, 1H)

For another NMR reading, some solid potassium carbonate was added into the DMSO solution of the 4-(4-bromo-2-fluoroanilino)-6-methoxy-7-1-methylpiperidin-4-ylmethoxy)quinazoline hydrochloride described above, in order to release the free base in the NMR tube. The NMR spectrum was then recorded again and showed only one form as described below:

$^1$H NMR Spectrum: ($DMSOd_6$; solid potassium carbonate) 1.3–1.45 (m, 2H); 1.75 (d, 2H); 1.7–1.9(m, 1H); 1.89 (t, 2H); 2.18 (s, 3H); 2.8 (d, 2H); 3.98 (s, 3H); 4.0 (d, 2H); 7.2 (s, 1H); 7.48 (d, 1H); 7.55 (t, 1H); 7.68 (d, 1H); 7.8 (s, 1H); 8.35 (s, 1H); 9.75 (s, 1H)

A sample of 4-(4-bromo-2-fluoroanilino-6-methoxy-7-(1-methylpiperidin-4-ylmethoxy)quinazoline (free base) was generated from the 4-(4-bromo-2-fluoroanilino)-6-methoxy-7-(1-methylpiperidin-4-ylmethoxy)quinazoline hydrochloride, (prepared as described above), as follows:

4-(4-Bromo-2-fluoroanilino)-6-methoxy-7-(methylpiperidin-4-ylmethoxyquinazoline hydrochloride (50 mg) was suspended in methylene chloride (2 ml) and was washed with saturated sodium hydrogen carbonate. The methylene chloride solution was dried ($MgSO_4$) and the volatiles were removed by evaporation to give 4-(4-bromo-2-fluoroanilino)-6-methoxy-7-(1-methylpiperidin-4-ylmethoxy)quinazoline (free base). The NMR of the free base so generated shows only one form as described below:

$^1$H NMR Spectrum: ($DMSOd_6$) 1.3–1.45 (m, 2H); 1.76 (d, 2H); 1.7–1.9(m, 1H); 1.9 (t, 2H); 2.19(s, 3H); 2.8(d, 2H); 3.95(s, 3H); 4.02(d, 2H); 7.2(s, 1H); 7.48(d, 1H); 7.55(t, 1H); 7.68 (dd, 1H); 7.8 (s, 1H); 8.38 (s, 1H); 9.55(br s, 1H)

For another NMR reading, some $CF_3COOD$ was added into the NMR DMSO solution of the 4-(4-bromo-2-fluoroanilino)-6-methoxy-7-(1-methylpiperidin-4-ylmethoxy)quinazoline (free base) described above and the NMR spectrum was recorded again. The spectrum of the protonated form of the 4-(4-bromo-2-fluoroanilino)-6-methoxy-7-(1-methylpiperidin-4-ylmethoxy)quinazoline trifluoroacetate salt so obtained shows the presence of two forms A and B in a ratio A:B of approximately 9:1.

$^1$H NMR Spectrum: ($DMSOd_6$; $CF_3COOD$) 1.5–1.7 (m, form A 2H); 1:93 (br s, form B 4H); 2.0–2.1 (d, form A 2H); 2.17 (br s, form A 1H); 2.35 (br s, form B1H); 2.71 (s, form A 3H); 2.73 (s, form B 3H); 2.97–3.09 (t, form A 2H); 3.23 (br s, form B 2H); 3.34 (br s, form B 2H); 3.47–3.57 (d, form A 2H); 4.02 (s, 3H); 4.15 (d, form A 2H); 4.30 (d, form B 2H); 7.2 (s, 1H); 7.3–7.5 (m, 2H); 7.6 (d, 1H); 7.9 (s, 1H); 8.7 (s, 1H)

The starting material was prepared as follows:

1-tert-Butoxycarbonyl-4-(4-methylphenylsulphonyloxymethyl)piperidine (40 g, 0.11 mol), (prepared as described for the starting material in Example 1), was added to a suspension of ethyl 4-hydroxy-3-methoxybenzoate (19.6 g, 0.1 mol) and potassium carbonate (28 g, 0.2 mol) in dry DMF (200 ml). After stirring at 95° C. for 2.5 hours, the mixture was cooled to ambient temperature and partitioned between water and ethyl acetate/ether. The organic layer was washed with water, brine, dried ($MgSO_4$) and evaporated. The resulting oil was crystallised from petroleum ether and the suspension was stored overnight at 5° C. The solid was collected by filtration, washed with petroleum ether and dried under vacuum to give ethyl 4(1-(tert-butoxycarbonyl)piperidin-4-ylmethoxy)-3-methoxybenzoate (35 g, 89%).

m.p. 81–83° C.

MS (ESI): 416 $[MNa]^+$ $^1$H NMR Spectrum: ($CDCl_3$) 1.2–1.35(m, 2H); 1.4(t, 3H), 1.48(s, 9H), 1.8–1.9(d, 2H), 2.0–2.15(m, 2H); 2.75(t, 2H); 3.9(d, 2H); 3.95(s, 3H); 4.05–4.25(br s, 2H); 4.35(q, 2H); 6.85(d, 1H); 7.55(s, 1H); 7.65(d, 1H)

Elemental analysis: $C_{21}H_{31}NO_6$ 0.3 $H_2O$; Found C 63.4, H 8.0, N 3.5; Requires C 63.2, H 8.0, N 3.5%.

Formaldehyde (12M, 37% in water, 35 ml, 420 mmol) was added to a solution of ethyl 4-(1-(tert-butoxycarbonyl)piperidin-4-ylmethoxy)-3-methoxybenzoate (35 g, 89 mmol) in formic acid (35 ml). After stirring at 95° C. for 3 hours, the volatiles were removed by evaporation. The residue was dissolved in methylene chloride and 3M hydrogen chloride in ether (40 ml, 120 mmol) was added. After dilution with ether, the mixture was triturated until a solid was formed. The solid was collected by filtration, washed with ether and dried under vacuum overnight at 50° C. to give ethyl 3-methoxy-4-(1-methylpiperidin-4-ylmethoxy)benzoate (30.6 g, quant.).

MS (ESI): 308 $[MH]^+$ $^1$H NMR Spectrum: ($DMSOd_6$) 1.29(t, 3H); 1.5–1.7(m, 2H); 1.95(d, 2H); 2.0–2.15(br s, 1H) 2.72(s, 3H); 2.9–3.1(m, 2H); 3.35–3.5(br s, 2H); 3.85(s, 3H); 3.9–4.05(br s, 2H); 4.3(q, 2H), 7.1(d, 1H); 7.48(s, 1H); 7.6(d, 1H)

A solution of ethyl 3-methoxy-4-(1-methylpiperidin-4-ylmethoxy)benzoate (30.6 g, 89 mmol) in methylene chloride (75 ml) was cooled to 0–5° C. TFA (37.5 ml) was added followed by the dropwise addition over 15 minutes of a solution of fuming 24N nitric acid (7.42 ml, 178 mmol) in methylene chloride (15 ml). After completion of the addition, the solution was allowed to warm up and stirred at ambient temperature for 2 hours. The volatiles were removed under vacuum and the residue was dissolved in methylene chloride (50 ml). The solution was cooled to 0–5° C. and ether was added. The precipitate was collected by filtration, and dried under vacuum at 50° C. The solid was dissolved in methylene chloride (500 ml) and 3M hydrogen chloride in ether (30 ml) was added followed by ether (500 ml). The solid was collected by filtration and dried under vacuum at 50° C. to give ethyl 3-methoxy-4-(1-methylpiperidin-4-ylmethoxy)-6-nitrobenzoate (28.4 g, 82%).

MS (ESI): 353 $[MH]^+$

¹H NMR Spectrum: (DMSOd₆) 1.3(t, 3H); 1.45–1.65(m, 2H); 1.75–2.1(m, 3H); 2.75(s, 3H); 2.9–3.05(m, 2H); 3.4–3.5(d, 2H); 3.95(s, 3H); 4.05(d, 2H); 4.3(q, 2H); 7.32(s, 1H); 7.66(s, 1H)

A suspension of ethyl 3-methoxy-4-(1-methylpiperidin-4-ylmethoxy)-6-nitrobenzoate (3.89 g, 10 mmol) in methanol (80 ml) containing 10% platinum on activated carbon (50% wet) (389 mg) was hydrogenated at 1.8 atmospheres pressure until uptake of hydrogen ceased. The mixture was filtered and the filtrate was evaporated. The residue was dissolved in water (30 ml) and adjusted to pH 10 with a saturated solution of sodium hydrogen carbonate. The mixture was diluted with ethyl acetate/ether (1/1) and the organic layer was separated. The aqueous layer was further extracted with ethyl acetate/ether and the organic layers were combined. The organic layers were washed with water, brine, dried (MgSO₄), filtered and evaporated. The resulting solid was triturated in a mixture of ether/petroleum ether, filtered, washed with petroleum ether and dried under vacuum at 60° C. to give ethyl 6-amino-3-methoxy-4-(1-methylpiperidin-4-ylmethoxy)benzoate (2.58 g, 80%).

m.p. 111–112° C.

MS (ESI): 323 [MH]⁺

¹H NMR Spectrum: (CDCl₃) 1.35(t, 3H); 1.4–1.5(m, 2H); 1.85(m, 3H); 1.95(t, 2H); 2.29(s, 3H); 2.9(d, 2H); 3.8(s, 3H); 3.85(d, 2H); 4.3(q, 2H); 5.55(br s, 2H); 6.13(s, 1H); 7.33(s, 1H)

Elemental analysis: $C_{17}H_{26}N_2O_4$ 0.2 $H_2O$; Found C 62.8, H 8.5, N 8.3; Requires C 62.6, H 8.2, N 8.6%.

A solution of ethyl 6-amino-3-methoxy-4-(1-methylpiperidin-4-ylmethoxy)benzoate (16.1 g, 50 mmol) in 2-methoxyethanol (160 ml) containing formamidine acetate (5.2 g, 50 mmol) was heated at 115° C. for 2 hours. Formamidine acetate (10.4 g, 100 mmol) was added in portions every 30 minutes over 4 hours. Heating was prolonged for 30 minutes after the last addition. After cooling, the volatiles were removed under vacuum. The solid was dissolved in ethanol (100 ml) and methylene chloride (50 ml). The precipitate was removed by filtration and the filtrate was concentrated to a final volume of 100 ml. The suspension was cooled to 5° C. and the solid was collected by filtration, washed with cold ethanol followed by ether and dried under vacuum overnight at 60° C. to give 6-methoxy-7-(1-methylpiperidin-4-ylmethoxy)-3,4-dihydroquinazolin-4-one (12.7 g, 70%).

MS (ESI): 304 [MH]⁺

¹H NMR Spectrum: (DMSOd₆) 1.25–1.4(m, 2H); 1.75(d, 2H); 1.9(t, 1H); 1.9(s, 3H); 2.16(s, 2H); 2.8(d, 2H); 3.9(s, 3H); 4.0(d, 2H); 7.11(s, 1H); 7.44(s, 1H); 7.97(s, 1H)

A solution of 6-methoxy-7-(1-methylpiperidin-4-ylmethoxy)-3,4-dihydroquinazolin-4-one (2.8 g, 9.24 mmol) in thionyl chloride (28 ml) containing DMF (280 µl) was heated at reflux at 85° C. for 1 hour. After cooling, the volatiles were removed by evaporation. The precipitate was triturated with ether, filtered, washed with ether and dried under vacuum. The solid was dissolved in methylene chloride and saturated aqueous sodium hydrogen carbonate was added. The organic layer was separated, washed with water, brine, dried (MgSO₄) and evaporated to give 4-chloro-6-methoxy-7-(1-methylpiperidin-4-ylmethoxy)quinazoline (2.9 g, 98%).

MS (ESI): 322 [MH]⁺

¹H NMR Spectrum: (DMSOd₆) 1.3–1.5(m, 2H); 1.75–1.9 (m, 3H); 2.0(t, 1H); 2.25(s, 2H); 2.85(d, 2H); 4.02(s, 3H); 4.12(d, 2H); 7.41(s, 1H); 7.46(s, 1H); 8.9(s, 1H)

Alternatively, the 6-methoxy-7-(1-methylpiperidin-4-ylmethoxy)-3,4-dihydroquinazolin-4-one can be prepared as follows:

Sodium hydride (1.44 g of a 60% suspension in mineral oil, 36 mmol) was added in portions over 20 minutes to a solution of 7-benzyloxy-6-methoxy-3,4-dihydroquinazolin-4-one (8.46 g, 30 mmol), (prepared, for example, as described in WO 97/22596, Example 1), in DMF (70 ml) and the mixture was stirred for 1.5 hours. Chloromethyl pivalate (5.65 g, 37.5 mmol) was added in portions and the mixture stirred for 2 hours at ambient temperature. The mixture was diluted with ethyl acetate (100 ml) and poured onto ice/water (400 ml) and 2N hydrochloric acid (4 ml). The organic layer was separated and the aqueous layer extracted with ethyl acetate, the combined extracts were washed with brine, dried (MgSO₄) and the solvent removed by evaporation. The residue was triturated with a mixture of ether and petroleum ether, the solid was collected by filtration and dried under vacuum to give 7-benzyloxy-6-methoxy-3-((pivaloyloxy)methyl)-3,4-dihydroquinazolin-4-one (10 g, 84%).

¹H NMR Spectrum: (DMSOd₆) 1.11(s, 9H); 3.89(s, 3H); 5.3(s, 2H); 5.9(s, 2H); 7.27(s, 1H); 7.35(m, 1H); 7.47(t, 2H); 7.49(d, 2H); 7.51(s, 1H); 8.34(s, 1H)

A mixture of 7-benzyloxy-6-methoxy-3-((pivaloyloxy)methyl)-3,4-dihydroquinazolin-4-one (7 g, 17.7 mmol) and 10% palladium-on-charcoal catalyst (700 mg) in ethyl acetate (250 ml), DMF (50 ml), methanol (50 ml) and acetic acid (0.7 ml) was stirred under hydrogen at atmospheric pressure for 40 minutes. The catalyst was removed by filtration and the solvent removed from the filtrate by evaporation. The residue was triturated with ether, collected by filtration and dried under vacuum to give 7-hydroxy-6-methoxy-3-((pivaloyloxy)methyl)-3,4-dihydroquinazolin-4-one (4.36 g, 80%).

¹H NMR Spectrum: (DMSOd₆) 1.1(s, 9H); 3.89(s, 3H); 5.89(s, 2H); 7.0(s, 1H); 7.48(s, 1H); 8.5(s, 1H)

Triphenylphosphine (1.7 g, 6.5 mmol) was added under nitrogen to a suspension of 7-hydroxy-6-methoxy-3-((pivaloyloxy)methyl)-3,4-dihydroquinazolin-4-one (1.53 g, 5 mmol) in methylene chloride (20 ml), followed by the addition of 1-(tert-butoxycarbonyl)-4-(hydroxymethyl)piperidine (1.29 g, 6 mmol), (prepared as described for the starting material in Example 1), and by a solution of diethyl azodicarboxylate (1.13 g, 6.5 mmol) in methylene chloride (5 ml). After stirring for 30 minutes at ambient temperature, the reaction mixture was poured onto a column of silica and was eluted with ethyl acetate/petroleum ether (1/1 followed by 6/5, 6/4 and 7/3). Evaporation of the fractions containing the expected product led to an oil that crystallised following trituration with pentane. The solid was collected by filtration and dried under vacuum to give 7-(1(tert-butoxycarbonyl)piperidin-4-ylmethoxy)-6-methoxy-3-((pivaloyloxy)methyl)-3,4-dihydroquinazolin-4-one (232 g, 92%).

MS—ESI: 526 [MNa]⁺

¹H NMR Spectrum: (CDCl₃) 1.20 (s, 9H), 1.2–1.35 (m, 2H), 1.43 (s, 9H), 1.87 (d, 2H), 2.05–2.2 (m, 1H), 2.75 (t, 2H), 3.96 (d, 2H), 3.97 (s, 3H), 4.1–4.25 (br s, 2H), 5.95 (s, 2H), 7.07 (s, 1H), 7.63 (s, 1H), 8.17 (s, 1H)

Elemental analysis: $C_{26}H_{37}N_3O_7$; Found C 61.8, H 7.5, N 8.3; Requires C 62.0, H 7.4, N 8.3%.

A solution of 7-(1-(tert-butoxycarbonyl)piperidin-4-ylmethoxy)-6-methoxy-3-((pivaloyloxy)methyl)-3,4-dihydroquinazolin-4-one (2.32 g, 4.6 mmol) in methylene chloride (23 ml) containing TFA (5 ml) was stirred at ambient temperature for 1 hour. The volatiles were removed under vacuum. The residue was partitioned between ethyl acetate and sodium hydrogen carbonate. The organic solvent was removed under vacuum and the residue was filtered. The precipitate was washed with water, and dried under vacuum. The solid was azeotroped with toluene and dried under vacuum to give 6-methoxy-7-(piperidin-4-ylmethoxy)-3-((pivaloyloxy)methyl)-3,4-dihydroquinazolin-4-one (1.7 g, 92%).

MS—ESI: 404 [MH]$^+$ $^1$H NMR Spectrum: (DMSOd$_6$; CF$_3$COOD) 1.15 (s, 9H), 1.45–1.6 (m, 2H), 1.95 (d, 2H), 2.1–2.25 (m, 1H), 2.95 (t, 2H), 3.35 (d, 2H), 3.95 (s, 3H), 4.1 (d, 2H), 5.95 (s, 2H), 7.23 (s, 1H), 7.54 (s, 1H), 8.45 (s, 1H)

A 37% aqueous solution of formaldehyde (501 μl, 6 mmol) followed by sodium cyanoborohydride (228 mg, 3.6 mmol) were added in portions to a solution of 6-methoxy-7-(piperidin-4-ylmethoxy)-3-((pivaloyloxy)methyl)-3,4-dihydroquinazolin-4-one (1.21 g, 3 mmol) in a mixture of THF/methanol (10 ml/10 ml). After stirring for 30 minutes at ambient temperature, the organic solvents were removed under vacuum and the residue was partitioned between methylene chloride and water. The organic layer was separated, washed with water and brine, dried (MgSO$_4$) and the volatiles were removed by evaporation. The residue was triturated with ether and the resulting solid was collected by filtration, washed with ether and dried under vacuum to give 6-methoxy-7-(1-methylpiperidin-4-ylmethoxy)-3-((pivaloyloxy)methyl)-3,4-dihydroquinazolin-4-one (1.02 g, 82%).

MS—ESI: 418[MH]$^+$ $^1$H NMR Spectrum: (CDCl$_3$) 1.19 (s, 9H), 1.4–1.55 (m, 2H), 1.9 (d, 2H), 2.0 (t, 2H), 1.85–2.1 (m, 1H), 2.3 (s, 3H), 2.92 (d, 2H), 3.96 (s, 3H), 3.99 (d, 2H), 5.94 (s, 2H), 7.08 (s, 1H), 7.63 (s, 1H), 8.17 (s, 1H)

A saturated solution of ammonia in methanol (14 ml) was added to a solution of 6-methoxy-7-(1-methylpiperidin-4-ylmethoxy)-3-((pivaloyloxy)methyl)-3,4-dihydroquinazolin-4-one (1.38 g, 3.3 mmol) in methanol (5 ml). After stirring for 20 hours at ambient temperature, the suspension was diluted with methylene chloride (10 ml). The solution was filtered. The filtrate was evaporated under vacuum and the residue was triturated with ether, collected by filtration, washed with ether and dried under vacuum to give 6-methoxy-7-(1-methylpiperidin-4-ylmethoxy)-3,4-dihydroquinazolin-4-one (910 mg, 83%).

MS—ESI: 304 [MH]$^+$ $^1$H NMR Spectrum: (DMSOd$_6$) 1.3–1.45 (m, 2H), 1.75 (d, 2H), 1.7–1.85 (m, 1H), 1.9 (t, 2H), 2.2 (s, 3H), 2.8 (d, 2H), 3.9 (s, 3H), 4.0 (d, 2H), 7.13 (s, 1H), 7.45 (s, 1H), 7.99 (s, 1H)

EXAMPLE 3a 3.5M Hydrogen chloride in ethanol (75 μl, 0.26 mmol) was added to a suspension of 4-chloro-6-methoxy-7-(1-methylpiperidin-4-ylmethoxy)quinazoline (80 mg, 0.25 mmol), (prepared as described for the starting material in Example 2c), in isopropanol (3 ml), the mixture was heated to 50° C. and 4-chloro-2-fluoroaniline (44 mg, 0.3 mmol) was added. The mixture was heated at reflux for 30 minutes. After cooling, the mixture was diluted with ether (3 ml). The precipitate was collected by filtration, washed with ether and dried under vacuum to give 4-(4-chloro-2-fluoroanilino)-6-methoxy-7-(1-methylpiperidin ylmethoxy)quinazoline hydrochloride (105 mg, 82%).

MS—ESI: 431–433 [MH]$^+$

The NMR spectrum of the protonated form of 4-(4-chloro-2-fluoroanilino)-6-methoxy-7-(1-methylpiperidin-4-ylmethoxy)quinazoline hydrochloride shows the presence of two forms A and B in a ratio A:B of approximately 9:1.

$^1$H NMR Spectrum: (DMSOd$_6$; CF$_3$COOD) 1.55–1.7 (m, form A 2H), 1.85–2.0 (m, form B 4H), 2.05 (d, form A 2H), 2.1–2.2 (m, form A 1H), 2.35 (s, 3H); 2.79 (s, form A 3H), 2.82 (s, form B 3H), 3.03 (t, form A 2H), 3.2–3.3 (m, form B 2H); 3.3–3.4 (m, form B 2H), 3.52 (d, form A 2H), 4.02 (s, 3H), 4.13 (d, form A 2H), 4.3 (d, form B 2H), 7.41 (s, 1H), 7.47 (dd, 1H), 7.63 (t, 1H), 7.69 (dd, 1H), 8.19 (s, 1H), 8.88 (s, 1H)

Elemental analysis: C$_{22}$H$_{24}$N$_4$O$_2$ClF 0.4 H$_2$O 2 HCl; Found C 51.8, H 5.6, N 10.9; Requires C 51.7, H 5.3, N 11.0%.

EXAMPLE 3b

An alternative method of preparation is as follows:

Triphenylphosphine (615 mg, 2.3 mmol) followed by diethyl azodicarboxylate (369 μl, 2.3 mmol) were added to a solution of 4-hydroxymethyl-1-methylpiperidine (151 mg, 1.1 mmol), (J Med. Chem 1973, 16, 156), and 4-(4-chloro-2-fluoroanilino)-7-hydroxy-6-methoxyquinazoline (250 mg, 0.78 mmol), (prepared as described for the starting material in Example 7), in methylene chloride (5 ml). After stirring for 30 minutes at ambient temperature, 4-hydroxymethyl-1-methylpiperidine (151 mg, 0.39 mmol), triphenylphosphine (102 mg, 0.39 mmol) and diethyl azodicarboxylate (61 μl, 0.39 mmol) were added. After stirring for 15 minutes, the volatiles were removed under vacuum and the residue was purified by column chromatography eluting with methylene chloride/acetonitrile/methanol (70/10/20 followed by 75/5/20 and 80/0/20). The fractions containing the expected product were combined and the volatiles were removed by evaporation. The residue was dissolved in a mixture of methylene chloride and methanol and 5M hydrogen chloride in isopropanol was added. The suspension was concentrated and the solid was collected by filtration, washed with ether and dried under vacuum to give 4-(4-chloro-2-fluoroanilino)-6-methoxy-7-(1-methylpiperidin-4-ylmethoxy) quinazoline hydrochloride (16 mg, 4%).

EXAMPLE 4

Under argon, sodium hydride (60%, 372 mg, 9.3 mmol) was added to a solution of 4-bromo-2,6-difluoroaniline (1.67 g, 8.08 mmol) in DMF. After stirring for 30 minutes at ambient temperature, 4-chloro-6-methoxy-7-(1-methylpiperidin-4-ylmethoxy)quinazoline (1.3 g, 4.04 mmol) was added and stirring was continued for a further 20 hours. The mixture was poured onto water (130 ml) and extracted with ethyl acetate. The organic layers were washed with water, brine, dried (MgSO$_4$) and the volatiles were removed by evaporation. The residue was purified by column chromatography on silica, eluting with methylene chloride/methanol (95/5) followed by methylene chloride/methanol containing ammonia (1%) (90/10). The fractions containing the expected product were combined and evaporated. The residue was triturated with ether, collected by filtration, washed with ether and dried under vacuum at 50° C. to give 4-(bromo-2,6-difluoroanilino)-6-methoxy-7-(1-methylpiperidin-4-ylmethoxy)quinazoline (1.4 g, 70%).

MS—ESI: 493–495 [MH]$^+$ $^1$H NMR Spectrum: (DMSOd$_6$) 1.3–1.45 (m, 2H), 1.8 (d, 2H), 1.7–1.9 (m, 1H), 1.9 (t, 2H), 2.17 (s, 3H), 2.8 (d, 2H), 3.95 (s, 3H), 4.02 (d, 2H), 7.2 (s, 1H), 7.63 (s, 1H), 7.6 (s, 1H), 7.82 (s, 1H), 8.35 (s, 1H)

Elemental analysis: $C_{22}H_{23}N_4O_2BrF_2$; Found C 53.8, H 4.8, N 11.3; Requires C 53.6, H 4.7, N 11.4%.

EXAMPLE 5

Using an analogous procedure to that described in Example 4,4-chloro-6-methoxy-7-(1-methylpiperidin-4-ylmethoxy)quinazoline (246 mg, 0.764 mmol), (prepared as described for the starting material in Example 2c), was reacted with 4-chloro-2,6-difluoroaniline (250 mg, 1.53 mmol), (see WO 97/30035 Example 15), in DMF (9 ml) and in the presence of sodium hydride (60%, 76.5 mg, 1.9 mmol) to give 4-(4-chloro-2,6-difluoroanilino-6-methoxy-7-(1-methylpiperidin-4-ylmethoxy)quinazoline (210 mg, 61%).

MS—ESI: 449–451 $[MH]^+$ $^1$H NMR Spectrum: $(DMSOd_6)$ 1.3–1.45 (m, 2H), 1.8 (d, 2H)—1.7–1.9 (m, 1H), 1.9 (t, 2H), 2.2 (s, 3H), 2.8 (d, 2H), 3.96 (s, 3H), 4.02 (d, 2H), 7.21 (s, 1H), 7.52 (s, 1H), 7.54 (s, 1H), 7.82 (s, 1H), 8.35 (s, 1H)

Elemental analysis: $C_{22}H_{23}N_4O_2ClF_2$; Found C 59.0, H 5.3, N 12.5; Requires C 58.9, H 5.2, N 12.5%.

The starting material was prepared as follows:

4-Chloro-2,6-difluoroaniline hydrochloride (see WO 97/30035 Example 15) was partitioned between methylene chloride and water and aqueous sodium hydrogen carbonate was added until the pH of the aqueous layer was approximately 9. The organic layer was separated, washed with brine, dried ($MgSO_4$) and evaporated to give 4-chloro-2,6-difluoroaniline free base.

EXAMPLE 6

A suspension of 4-chloro-6-methoxy-7-(1-methylpiperidin-4-ylmethoxy)quinazoline (200 mg, 0.622 mmol), (prepared as described for the starting material in Example 2c) and 2-fluoro-4-methylaniline (94 mg, 0.764 mmol) in isopropanol (5 ml) containing 6.2M hydrogen chloride in isopropanol (110 µl) was stirred at 80° C. for 1.5 hours. After cooling, the precipitate was collected by filtration, washed with isopropanol, followed by ether and dried under vacuum. The solid was purified by column chromatography, eluting with methylene chloride/methanol (90/10) followed by 5% ammonia in methanol/methylene chloride (10/90). Evaporation of the fractions containing the expected product gave 4-(2-fluoro-4-methylanilin)-6-methoxy-7-(1-methylpiperidin-4-ylmethoxy)quinazoline (170 mg, 61%).

MS—ESI: 411 $[MH]^+$ $^1$H NMR Spectrum: $(DMSOd_6)$ 1.3–1.45 (m, 2H), 1.8 (d, 2H), 1.7–1.9 (m, 1H), 1.9 (t, 2H), 2.2 (s, 3H), 2.35 (s, 3H), 2.8 (d, 2H), 3.95 (s, 3H), 4.01 (d, 2H), 7.1 (d, 1H), 7.13 (d, 1H), 7.16 (s, 1H), 7.4 (t, 1H), 7.81 (s, 1H), 8.32 (s, 1H), 9.4 (s, 1H)

Elemental analysis: $C_{22}H_{27}N_4O_2F$ 0.3 $H_2$); Found C 66.5, H 6.7, N 13.7; Requires C 66.4, H 6.7 N 13.5%.

EXAMPLE 7

1-tert-Butoxycarbonyl-4-hydroxymethylpiperidine (590 mg, 2.75 mmol), (prepared as described for the starting material in Example 1), followed by triphenylphosphine (1.2 g, 4.58 mmol) and diethyl azodicarboxylate (0.72 ml, 4.58 mmol) were added to a solution of 4-(4-chloro-2-fluoroanilino)-7-hydroxy-6-methoxyquinazoline (585 mg, 1.83 mmol) in methylene chloride (20 ml). After stirring for 1 hour at ambient temperature, further triphenylphosphine (239 mg, 0.91 mmol) and diethyl azodicarboxylate (0.14 ml, 0.91 mmol) were added. After stirring for 1.5 hours, the volatiles were removed under vacuum and the residue was purified by column chromatography eluting with ethyl acetate/methylene chloride (1/1). The crude product was used directly in the next step.

A solution of the crude product in methylene chloride (15 ml) containing TFA (4.5 ml) was stirred at ambient temperature for 1.5 hours. The volatiles were removed under vacuum. The residue was partitioned between water and ethyl acetate. The aqueous layer was adjusted to pH 9.5 with 2N sodium hydroxide. The organic layer was separated, washed with water, followed by brine, dried ($MgSO_4$) and evaporated to give 4-(4-chloro-2-fluoroanilino)-6-methoxy-7-piperidin-4-ylmethoxy)quinazoline.

MS—ESI: 417–419 $[MH]^+$ $^1$H NMR Spectrum: $(DMSOd_6)$ 1.1–1.3 (m, 2H), 1.75 (d, 2H), 1.85–2.0 (br s, 1H), 2.55 (d, 2H), 2.95 (d, 2H), 3.95 (s, 3H), 4.0 (d, 2H), 7.2 (s, 1H), 7.35 (dd, 1H), 7.55 (dd, 1H), 7.6 (t, 1H), 7.8 (s, 1H), 8.35 (s, 1H), 9.55 (s, 1H)

The hydrochloride salt was made as follows:

4-(4-Chloro-2-fluoroanilino)-6-methoxy-7-(piperidin-4-ylmethoxy)quinazoline was dissolved in a mixture of methanol/methylene chloride and 6M hydrogen chloride in ether was added. The volatiles were removed under vacuum, the residue was triturated with ether, collected by filtration, washed with ether and dried under vacuum to give 4-(4-chloro-2-fluoro)-6-methoxy-7-(piperidin-4-ylmethoxy) quinazoline hydrochloride (390 mg, 47% over 2 steps).

Elemental analysis: $C_{21}H_{22}O_2N_4ClF$ 2.25 HCl; Found C 50.4, H 5.2, N 11.0; Requires C 50.6, H 4.9, N 11.2%.

The starting material was prepared as follows:

A solution of 7-benzyloxy-4-chloro-6-methoxyquinazoline hydrochloride (1.2 g, 4 mmol), (prepared as described in WO 97/22596, Example 1), and 4-chloro-2-fluoroaniline (444 µl, 4 mmol) in 2-propanol (40 ml) was heated at reflux for 1.5 hours. After cooling, the precipitate was collected by filtration, washed with 2-propanol then ether and dried under vacuum to give 7-benzyloxy-4-(4-chloro-2-fluoroanilino)-6-methoxyquinazoline hydrochloride (1.13 g, 64%).

m.p. 239–242° C.

$^1$H NMR Spectrum: $(DMSOd_6)$ 4.0(s, 3H); 5.36(s, 2H); 7.39–7.52(m, 9H); 8.1(s, 1H); 8.75(s, 1H)

MS—ESI: 410$[MH]^+$

Elemental analysis: $C_{22}H_{17}N_3O_2ClF$ 1 HCl; Found C 59.2, H 4.3, N 9.4; Requires C 59.2, H 4.1, N 9.4%.

A solution of 7-benzyloxy-4-(4-chloro-2-fluoroanilino)-6-methoxyquinazoline hydrochloride (892 mg, 2 mmol) in TFA (10 ml) was heated at reflux for 50 minutes. After cooling, the mixture was poured onto ice. The precipitate was collected by filtration, dissolved in methanol (10 ml) and basified to pH 11 with aqueous ammonia. After concentration by evaporation, the solid product was collected by filtration, washed with water then ether and dried under vacuum to give 4-(4-chloro-2-fluoroanilino)-7-hydroxy-6-methoxyquinazoline as a yellow solid (460 mg, 72%).

m.p. 141–143° C.

MS—ESI: 320–322 $[MH]^+$ $^1$H NMR Spectrum: $(DMSOd_6)$ 3.95(s, 3H); 7.05(s, 1H); 7.35(d, 1H); 7.54–7.59(m, 2H); 7.78(s, 1H); 8.29(s, 1H)

EXAMPLE 8

A suspension of 7-(1-(tert-butoxycarbonyl)piperidin-4-ylmethoxy)-4-(2-fluoro-4-methylanilino)-6-methoxyquinazoline (318 mg, 0.64 mmol) in methylene chloride (5 ml) containing TFA (2.5 ml) was stirred at ambient temperature for 2 hours. The volatiles were removed under vacuum and the residue was partitioned between methylene chloride and water. The aqueous layer was adjusted to pH 10–11. The organic layer was separated, washed with water, brine, dried (MgSO$_4$) and the volatiles were removed by evaporation to give 4-(2-fluoro-4-methylanilino)-6-methoxy-7-(piperidin-4-ylmethoxy)quinazoline (220 mg, 87%).

MS—ESI: 397 [MH]+

$^1$H NMR Spectrum: (DMSOd$_6$) 1.15–1.3 (m, 2H); 1.75 (d, 2H); 1.85–2.0 (m, 1H); 2.4 (s, 3H); 3.0 (d, 2H); 3.3–3.4 (d, 2H); 3.95 (s, 3H); 4.0 (d, 2H); 7.04 (d, 1H); 7.15 (d, 1H); 7.17 (s, 1H); 7.4 (t, 1H); 7.8 (s, 1H); 8.3 (s, 1H); 9.4 (s, 1H)

The starting material was prepared as follows:

Using an analogous procedure to that described in Example 6, 7-benzyloxy-4-chloro-6-methoxyquinazoline hydrochloride (1.55 g, 5.15 mmol), (prepared, for example, as described in WO 97/22596, Example 1), was reacted with 2-fluoro-4-methylaniline (700 mg, 5.67 mmol) in isopropanol (90 ml) containing 6.2M hydrogen chloride in isopropanol (80 µl, 0.51 mmol) to give 7-benzyloxy-4-(2-fluoro-4-methylanilino)-6-methoxyquinazoline hydrochloride (2 g, 91%).

MS—ESI: 390 [MH]$^+$ $^1$H NMR Spectrum: (DMSOd$_6$) 2.4 (s, 3H), 4.01 (s, 3H), 7.15 (d, 1H), 7.25 (d, 1H), 7.35–7.6 (m, 7H), 8.3 (s, 1H), 8.78 (s, 1H)

A solution of 7-benzyloxy-4-(2-fluoro-4-methylanilino)-6-methoxyquinazoline hydrochloride (2 g, 4.7 mmol) in TFA (20 ml) was heated at 80° C. for 5 hours and stirred at ambient temperature overnight. The volatiles were removed under vacuum and the residue was suspended in water (50 ml). Solid sodium hydrogen carbonate was added until the pH was approximately 7. The precipitate was then collected by filtration, washed with water and dried under vacuum. The solid was purified by column chromatography eluting with methanol/methylene chloride (5/95). After removal of the solvent by evaporation, the solid was triturated with ether, collected by filtration, washed with ether and dried under vacuum to give 4-(2-fluoro-4-methylanilino)-7-hydroxy-methoxyquinazoline (1.04 g, 74%).

MS—ESI: 300 [MH]$^+$ $^1$H NMR Spectrum: (DMSOd$_6$) 2.4 (s, 3H), 4.0 (s, 3H), 7.15 (d, 1H), 7.22 (s, 1H), 7.25 (d, 1H), 7.41 (t, 1H), 8.05 (s, 1H), 8.7 (s, 1H), 11.0 (s, 1H), 11.5–11.8 (br s, 1H)

Triphenylphosphine (2.19 g, 8.36 mmol) was added to a suspension of 4-(2-fluoro-4-methylanilino)-7-hydroxy-6-methoxyquinazoline (1 g, 3.34 mmol) in methylene chloride (10 ml) cooled at 0° C., followed by 1-(tert-butoxycarbonyl)-4-hydroxymethylpiperidine (1.08 g, 5.01 mmol), (prepared as described for the starting material in Example 1), and diethyl azodicarboxylate (1.31 ml, 8.36 mmol). After stirring for 2 hours at ambient temperature, the volatiles were removed under vacuum. The residue was purified by column chromatography eluting with methylene chloride/methanol (2/98). After removal of the solvent by evaporation, the residue was triturated with ether, collected by filtration, washed with ether and dried under vacuum to give 7-(1-(tert-butoxycarbonyl)piperidin-4-ylmethoxy)-4-(2-fluoro-4-methylanilino)-6-methoxyquinazoline (327 mg, 20%).

MS—ESI: 497 [MH]$^+$ $^1$H NMR Spectrum: (DMSOd$_6$) 1.15–1.3 (m, 2H); 1.45 (s, 9H); 1.8 (d, 2H); 2.0–2.1 (m, 1H); 2.4 (s, 3H); 2.75–2.9 (br s, 2H); 3.95 (s, 3H); 4.0 (br s, 2H); 4.05 (d, 2H); 7.1 (d, 1H); 7.15 (d, 1H); 7.2 (s, 1H); 7.4 (t, 1H); 7.85 (t, 1H); 8.32 (s, 1H); 9.45 (s, 1H)

EXAMPLE 9

A solution of 4-(4-bromo-2,6-difluoroanilino)-7-(1-(tert-butoxycarbonyl)piperidin-4-ylmethoxy)-6-methoxyquinazoline (578 mg, 1 mmol) in methylene chloride (10 ml) containing TFA (4 ml) was stirred at ambient temperature for 2 hours. The volatiles were removed under vacuum and the residue was suspended in water. The aqueous layer was adjusted to approximately pH 10 and was extracted with methylene chloride. The organic layer was washed with water, brine, dried (MgSO$_4$) and the volatiles were removed by evaporation. The residue was triturated with ether and dried under vacuum to give 4-(4-bromo-2,6-difluoroanilino)-6-methoxy-7-(piperidin-4-ylmethoxy)quinazoline (110 mg, 23%).

MS—ESI: 479–481 [MH]$^+$ $^1$H NMR Spectrum: (DMSOd$_6$) 1.15–1.3 (m, 2H); 1.75 (d, 2H); 1.85–2.0 (br s, 1H); 2.5 (d, 2H); 3.0 (d, 2H); 3.97 (s, 3H); 4.0 (d, 2H); 7.2 (s, 1H); 7.62 (d, 2H); 7.82 (s, 1H); 8.35 (s, 1H)

$^1$H NMR Spectrum: (DMSOd$_6$; CF$_3$COOD) 1.5–1.65 (m, 2H); 2.0 (d, 2H); 2.15–2.3 (br s, 1H); 3.0(t 2H); 3.4 (d, 2H); 4.02 (s, 3H); 4.15 (d, 2H); 7.4 (s, 1H); 7.75 (d, 2H); 8.1 (s, 1H); 8.92 (s, 1H)

The starting material was prepared as follows:

Sodium hydride (60%, 612 mg, 15.3 mmol) was added to a solution of 4-bromo-2,6-difluoroaniline (2.77 g, 6.65 mmol) in DMF (80 ml). After stirring for 30 minutes at ambient temperature, 7-benzyloxy-4-chloro-6-methoxyquinazoline (2 g, 6.65 mmol), (prepared, for example, as described in WO 97/22596, Example 1, but the free base was generated prior to use), was added and stirring was maintained for 4 hours. The mixture was partitioned between ethyl acetate and water (200 ml). The organic layer was separated, washed with water, brine, dried (MgSO$_4$) and the volatiles were removed by evaporation. The residue was triturated with isopropanol, collected by filtration, washed with ether and dried under vacuum to give 7-benzyloxy-4-(4-bromo-2,6-difluoroanilino)-6-methoxyquinazoline (1.95 g, 62%).

MS—ESI: 472–474 [MH]$^+$ $^1$H NMR Spectrum: (DMSOd$_6$) 3.94 (s, 3H), 5.3 (s, 2H), 7.3 (s, 1H), 7.4 (d, 1H), 7.45 (t, 2H), 7.5 (s, 1H), 7.55 (d, 1H), 7.65 (d, 2H), 7.85 (s, 1H), 8.35 (s, 1H), 9.4–9.6 (br s, 1H)

Using an analogous procedure to that described for the synthesis of the starting material in Example 8, 7-benzyloxy-4-(4-bromo-2,6-difluoroanilino)-6-methoxyquinazoline (1.9 g, 4.02 mmol) was reacted with TFA (20 ml) to give 4-(4-bromo-2,6-difluoroanilino)-7-hydroxy-6-methoxyquinazoline (1.5 g, 98%).

$^1$H NMR Spectrum: (DMSOd$_6$) 3.95 (s, 3H), 7.1 (s, 1H), 7.6 (s, 1H), 7.65 (s, 1H), 7.8 (s, 1H), 8.3 (s, 1H), 9.45 (br s, 1H), 10.5 (br s, 1H)

Using an analogous procedure to that described in the preparation of the starting material in Example 8, 4-(4-bromo-2,6-difluoroanilino)-7-hydroxy-6-methoxyquinazoline (1 g, 2.62 mmol) was reacted with 1-tert-butoxycarbonyl) 1-hydroxymethylpiperidine (845 mg, 3.93 mmol), (prepared as described for the starting material in Example 1), to give 4-(4-bromo-2,6-difluoroanilino)-7-(1-(tert-butoxycarbonyl)piperidin-4-ylmethoxy)-6-methoxyquinazoline (620 mg, 41%).

MS—ESI: 579–581 [MH]+

$^1$H NMR Spectrum: (DMSOd$_6$) 1.15–1.3 (m, 2H); 1.45 (s, 9H); 1.8 (d, 2H); 2.0–2.1 (m, 1H); 2.7–2.9 (m, 2H); 3.95 (s, 3H); 4.0 (br s, 2H); 4.05 (d, 2H); 7.22 (s, 1H); 7.65 (d, 2H); 7.85 (s, 1H); 8.35 (s, 1H); 9.4–9.6 (br s, 1H)

EXAMPLE 10

Using an analogous procedure to that described in Example 9, 7-(1-(tert-butoxycarbonyl)piperidin-4-yl-methoxy)-4-(4-chloro-2,6-difluoroanilino)-6-methoxyquinazoline (95 mg, 0.2 mmol) in methylene chloride (2 ml) was treated with TFA (800 μl) to give 4-(4-chloro-2,6-difluoroanilino)-6-methoxy-7-(piperidin-4-ylmethoxy)quinazoline (20 mg, 26%).

MS—ESI: 435–437 [MH]+

$^1$H NMR Spectrum: (DMSOd$_6$) 1.2–1.3 (m, 2H); 1.75 (d, 2H); 1.85–2.0 (br s, 1H); 2.5 (d, 2H); 3.0 (d, 2H); 3.97 (s, 3H); 4.0 (d, 2H); 7.2 (s, 1H); 752 (d, 2H); 7.85 (s, 1H); 8.35 (s, 1H)

The starting material was prepared as follows:

Using an analogous procedure to that described for the preparation of the starting material in Example 9, 7-benzyloxy-4-chloro-6-methoxyquinazoline (184 mg, 0.61 mmol), (prepared, for example, as described in WO 97/22596, Example 1, but the free base was generated prior to use), was reacted with 4-chloro-2,6-difluoroaniline (200 mg, 1.22 mmol) in the presence of sodium hydride (60%, 87 mg, 1.4 mmol) in DMF (8 ml) to give 7-benzyloxy-4-(4-chloro-2,6-difluoroanilino)-6-methoxyquinazoline (212 mg, 74%).

MS—ESI: 428 [MH]+

$^1$H NMR Spectrum: (DMSOd$_6$) 3.96 (s, 3H); 5.31 (s, 2H); 7.32 (s, 1H); 7.4 (d, 1H); 7.45 (t, 2H); 7.5–7.6 (m, 4H); 7.85 (s, 1H); 8.35 (br s, 1H); 9.55 (br s, 1H)

A solution of 7-benzyloxy-4-(4-chloro-2,6-difluoroanilino)-6-methoxyquinazoline (200 mg, 0.47 mmol) in TFA (3 ml) was stirred at 80° C. for 3 hours. After cooling, the volatiles were removed under vacuum and the residue was dissolved in water containing 5% methanol. The pH was adjusted to 8 with sodium hydrogen carbonate and the solid was collected by filtration and washed with water. The solid was solubilised in a mixture of ethyl acetate/methanol/methylene chloride (47/6/47). The volatiles were removed under vacuum to give 4-(4-chloro-2,6-difluoroanilino)-7-hydroxy-6-methoxyquinazoline (126 mg, 80%).

MS—ESI: 338 [MH]+

$^1$H NMR Spectrum: (DMSOd$_6$) 3.95 (s, 3H); 7.1 (s, 1H); 7.55 (d, 2H); 7.8 (s, 1H); 8.3 (s, 1H); 9.42 (br s, 1H)

Using an analogous procedure to that described for the preparation of the starting material in Example 9, 4-(4-chloro-2,6-difluoroanilino)-7-hydroxy-6-methoxyquinazoline (150 mg, 0.44 mmol) was reacted with 1-tert-butoxycarbonyl)-4-hydroxymethylpiperidine (150 mg, 0.88 mmol), (prepared as described for the starting material in Example 1), to give 7-(1-(tert-butoxycarbonyl)piperidin-4-yl-methoxy)-4-(4-chloro-2,6-difluoroanilino)-6-methoxyquinazoline (113 mg, 59%).

MS—ESI: 535[MH]+

$^1$H NMR Spectrum: (DMSOd$_6$) 1.15–1.3 (m, 2H); 1.45 (s, 9H); 1.8 (d, 2H); 2.0–2.1 (m, 1H); 2.7–2.9 (m, 2H); 3.95 (s, 3H); 4.0 (br s, 2H); 4.05 (d, 2H); 7.2 (s, 1H); 7.6 (m, 2H); 7.8 (s, 1H); 8.35 (s, 1H); 9.4–9.6 (br s, 1H)

EXAMPLE 11

The following illustrate representative pharmaceutical dosage forms containing the compound of formula I, or a pharmaceutically acceptable salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium stearate | 1.5 |

| (e) Injection I | (50 mg/ml) |
|---|---|
| Compound X | 5.0% w/v |
| 1 M Sodium hydroxide solution | 15.0% v/v |
| 0.1 M Hydrochloric acid (to adjust pH to 7.6) | |
| Polyethylene glycol 400 | 4.5% w/v |
| Water for injection to 100% | |

| (f) Injection II | 10 mg/ml |
|---|---|
| Compound X | 1.0% w/v |
| Sodium phosphate BP | 3.6% w/v |
| 0.1 M Sodium hydroxide solution | 15.0% v/v |
| Water for injection to 100% | |

| (g) Injection III | (1 mg/ml,buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note
The above formulations may be obtained by conventional procedures well known in the pharmaceutical art. The tablets (a)–(c) may be enteric coated by conventional means, for example to provide a coating of cellulose acetate phthalate.

The invention claimed is:
1. A quinazoline derivative of the formula I:

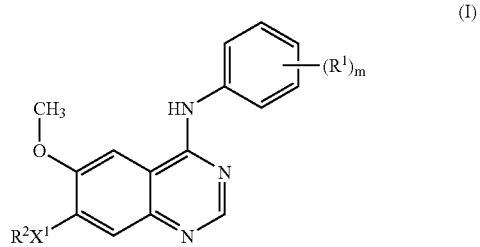

wherein:
m is an integer from 1 to 3;
$R^1$ represents halogeno or $C_{1-3}$alkyl;
$X^1$ represents —O—;
$R^2$ is selected from one of the following three groups:
 1) $C_{1-5}$alkyl$R^3$, wherein $R^3$ is piperidin-4-yl which may bear one or two substituents selected from hydroxy, halogeno, $C_{1-4}$alkyl, $C_{1-4}$hydroxyalkyl and $C_{1-4}$alkoxy;
 2) $C_{2-5}$alkenyl$R^3$, wherein $R^3$ is as defined herein;
 3) $C_{2-5}$alkynyl$R^3$, wherein $R^3$ is as defined herein;
and wherein any alkyl, alkenyl or alkynyl group may bear one or more substituents selected from hydroxy, halogeno and amino;
or a salt thereof.

2. The quinazoline derivative as claimed in claim 1 wherein the phenyl group of formula I together with the $(R^1)_m$ substituent:

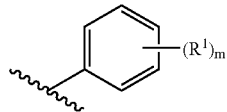

forms a group selected from 2-fluoro-4-methylphenyl, 4-chloro-2,6-difluorophenyl, 4-bromo-2,6-difluorophenyl, 4-chloro-2-fluorophenyl group and 4-bromo-2-fluorophenyl.

3. The quinazoline derivative as claimed in claim 1 wherein $R^2$ is $C_{1-5}$alkyl$R^3$, wherein $R^3$ is as defined in claim 1.

4. The quinazoline derivative as claimed in claim 1 wherein $R^2$ is piperidin-4-ylmethyl in which the piperidine ring may bear one or two substituents selected from $C_{1-4}$alkyl.

5. A quinazoline derivative of the formula II:

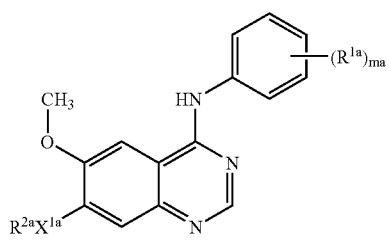

(II)

wherein:
ma is an integer from 1 to 3;
$R^{1a}$ represents halogeno or $C_{1-3}$alkyl;
$X^{1a}$ represents —O—;
$R^{2a}$ is selected from one of the following three groups:
 1) $C_{1-5}$alkyl$R^3$, wherein $R^3$ is piperidin-4-yl which may bear one or two substituents selected from hydroxy, halogeno, $C_{1-4}$alkyl, $C_{1-4}$hydroxyalkyl and $C_{1-4}$alkoxy;
 2) $C_{2-5}$alkenyl$R^3$, wherein $R^3$ is as defined herein;
 3) $C_{2-5}$alkynyl$R^3$, wherein $R^3$ is as defined herein;
or a salt thereof.

6. A quinazoline derivative selected from:
4-(4-chloro-2-fluoroanilino)-6-methoxy-7-(1-methylpiperidin-4-ylmethoxy)quinazoline,
4-(2-fluoro-4-methylanilino)-6-methoxy-7-(1-methylpiperidin-4-ylmethoxy)quinazoline,
4-(4-bromo-2-fluoroanilino)-6-methoxy-7-(1-methylpiperidin-4-ylmethoxy)quinazoline,
4-(4-chloro-2,6-difluoroanilino)-6-methoxy-7-(1-methylpiperidin-4-ylmethoxy)quinazoline,
4-(4-bromo-2,6-difluoroanilino)-6-methoxy-7-(1-methylpiperidin-4-ylmethoxy)quinazoline,
4-(4-chloro-2-fluoroanilino)-6-methoxy-7-(piperidin-4-ylmethoxy)quinazoline,
4-(2-fluoro-4-methylanilino)-6-methoxy-7-(piperidin-4-ylmethoxy)quinazoline,
4-(4-bromo-2-fluoroanilino)-6-methoxy-7-(piperidin-4-ylmethoxy)quinazoline,
4-(4-chloro-2,6-difluoroanilino)-6-methoxy-7-(piperidin-4-ylmethoxy)quinazoline, and
4-(4-bromo-2, 6-difluoroanilino)-6-methoxy-7-(piperidin-4-ylmethoxy)quinazoline,
or a salt thereof.

7. A quinazoline derivative selected from:
4-(4-chloro-2-fluoroanilino)-6-methoxy-7-(1-methylpiperidin-4-ylmethoxy)quinazoline,
4-(4-bromo-2-fluoroanilino)-6-methoxy-7-(1-methylpiperidin-4-ylmethoxy)quinazoline,
4-(4-chloro-2,6-difluoroanilino)-6-methoxy-7-(1-methylpiperidin-4-ylmethoxy)quinazoline, and
4-(4-bromo-2,6-difluoroanilino)-6-methoxy-7-(1-methylpiperidin-4-ylmethoxy)quinazoline,
or a salt thereof.

8. A quinazoline derivative selected from:
4-(4-bromo-2-fluoroanilino)-6-methoxy-7-(1-methylpiperidin-4-ylmethoxy)quinazoline or a salt thereof.

9. A quinazoline derivative as claimed in any one of claims 1–8 in the form of a pharmaceutically acceptable salt.

10. A process for the preparation of a quinazoline derivative of formula I, as defined in claim 1, or a salt thereof which comprises:
(a) the reaction of a compound of the formula III:

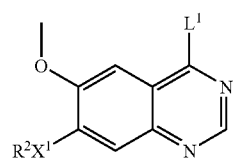

(III)

wherein $R^2$ and $X^1$ are as defined in claim 1 and $L^1$ is a displaceable moiety, with a compound of the formula IV:

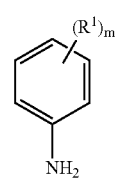

(IV)

wherein $R^1$ and m are as defined in claim 1;

(b) the reaction of a compound of the formula V:

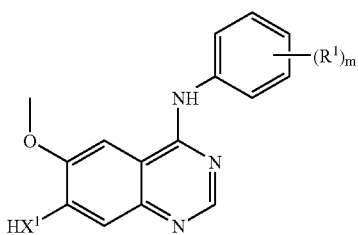

(V)

wherein m, $X^1$ and $R^1$ are as defined in claim 1 with a compound of formula VI:

$$R^2—L^1 \qquad (VI)$$

wherein $R^2$ is as defined in claim 1 and $L^1$ is as defined herein;

(c) the reaction of a compound of the formula VII:

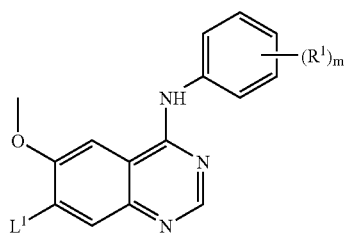

(VII)

with a compound of the formula VIII:

$$R^2—X^1—H \qquad (VIII)$$

wherein $R^1$, $R^2$, m and $X^1$ are as defined in claim 1 and $L^1$ is as defined herein; or (d) the deprotection of a compound of the formula IX:

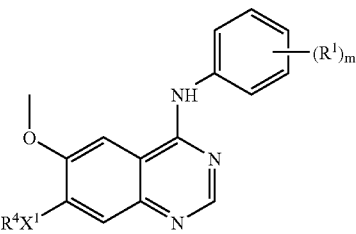

(IX)

wherein $R^1$, m and $X^1$ are as defined in claim 1, and $R^4$ represents a protected $R^2$ group wherein $R^2$ is as defined in claim 1 but additionally bears one or more protecting groups;

and when a pharmaceutically acceptable salt of a quinazoline derivative of formula I is required, reaction of the compound obtained with an acid or base whereby to obtain the desired pharmaceutically acceptable salt.

11. A pharmaceutical composition which comprises as active ingredient a compound of formula I as defined in any one of claims 1–8 or a pharmaceutically acceptable salt thereof, in association with a pharmaceutically acceptable excipient or carrier.

\* \* \* \* \*